United States Patent [19]
Riff et al.

[11] Patent Number: 5,351,696
[45] Date of Patent: Oct. 4, 1994

[54] METHOD AND APPARATUS FOR INTRACARDIAC ELECTROGRAM MORPHOLOGIC ANALYSIS

[75] Inventors: Kenneth M. Riff, Plymouth; Ray S. McDonald, Roseville; Michael J. German, Mounds View, all of Minn.

[73] Assignee: Medtronic, Inc., Minneapolis, Minn.

[21] Appl. No.: 52,359

[22] Filed: Apr. 23, 1993

[51] Int. Cl.⁵ .......................................... A61B 5/0452
[52] U.S. Cl. .................................................. 128/702
[58] Field of Search .................... 607/9; 128/702–705, 128/695–696

[56] References Cited

U.S. PATENT DOCUMENTS 3,616,971 11/1971 Harris ................................. 128/703

OTHER PUBLICATIONS

Ravelli et al, "Proceedings of Computers in Cardiology" Jeruslem, Israel, Sep. 19-27, 1989, pp. 502–504.
"Identification of Ventricular Tachycardia Using Intracavitary Ventricular Electrograms: Analysis of Time and Frequency Domain Patterns" by Lin et al. in Nov. 1988, Part 1, PACE, vol. 11.
"Atrial Electrogram Analysis: Antegrade Versus Retrograde", by McAlister et al., in Nov. 1988 Part II, vol. 11 PACE.
"Discrimination of Antegrade from Retrograde Atrial Electrograms for Physiologic Pacing", by Timmis et al., in PACE, vol. 11, Feb., 1988.
"Discrimination of Antegrade and Retrograde Atrial Depolarization by Electrogram Analysis", by Pannizzo, et al., in American Heart Journal, Oct., 1986.
"Detection of Pathological Tachycardia by Analysis of Electrogram Morphology", by Davis, et al., in PACE, vol. 9, Mar.-Apr., 1986.
"Ideal Atrial Lead Positioning to Detect Retrograde Atrial Depolarizationn by Digitization and Slope Analysis of the Atrial Electrogram", by Wainwright, et al., in PACE, vol. 7, Nov.–Dec., 1984, Part II.

*Primary Examiner*—William E. Kamm
*Attorney, Agent, or Firm*—Reed A. Duthler; Harold R. Patton

[57] ABSTRACT

A method and apparatus for morphologic analysis of an electrical signal, implementable in an implantable device such as a pacemaker, cardioverter, defibrillator or the like. The morphologic analysis uses a phase plane representation of the signal, where the signal and its first derivative are plotted along orthogonal axes. A magnitude signal corresponding to the magnitude component of the trajectory of the phase plane representation is generated and applied to a comparator. The comparator produces an activation signal when the magnitude signal exceeds a predetermined threshold. In response to the activation signal, a quadrant detector selectively applies the magnitude signal to one of four integrators, the selection of one integrator over the others being based at all times upon which quadrant of the phase plane the trajectory is in. When the magnitude decreases below a predetermined threshold, the activation signal is deasserted, whereupon the respective outputs from the four integrators may be interpreted as reflecting of the trajectory of the phase plane representation of the signal. In operation, a particular cardiac event to be detected is induced in a patient, and the resultant phase plane signals are examined to determine particular aspects of the phase plane signals which can be used as an indication that the particular event has occurred. The apparatus is then conditioned to recognize such aspects in subsequent phase plane signals, in order to provide an indication when such aspects are again present in the signals.

11 Claims, 17 Drawing Sheets

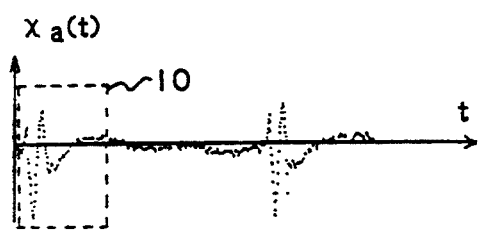 
FIG. 1a  FIG. 1b
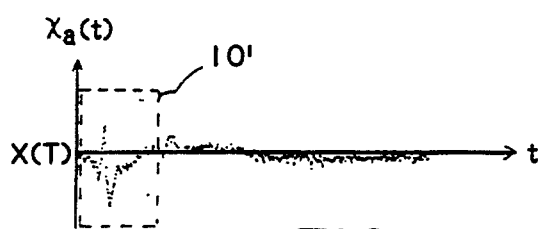 
FIG. 1c  FIG. 1d
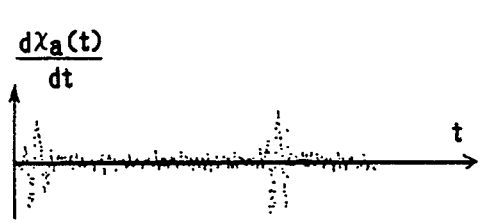 
FIG. 2a  FIG. 2b
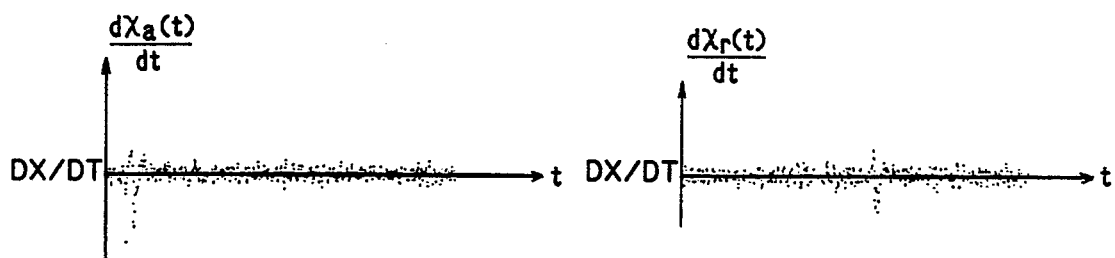
FIG. 2c  FIG. 2d

METHOD AND APPARATUS FOR INTRACARDIAC ELECTROGRAM MORPHOLOGIC ANALYSIS

FIELD OF THE INVENTION

This invention relates generally to the field of medical devices, and more particularly relates to an implantable medical device having circuitry for analyzing the morphology of intracardiac electrogram signals.

BACKGROUND OF THE INVENTION

Among the various types of devices for monitoring and/or therapeutically stimulating a patient's heart, a great many are known which are responsive to detected cardiac activity to operate in a particular manner. Perhaps the most common example of such a device is the so-called demand pacemaker, which is responsive to sensed electrical cardiac activity in either or both chambers of the heart, such that pacing pulses are delivered only in the absence of intrinsic cardiac activity. Implantable, cardiac defibrillators and cardioverters are also typically made responsive to sensed electrical cardiac activity.

For any device in which proper operation depends upon sensing and interpreting cardiac electrogram (EGM) signals, it is of course desirable to enable the device to accurately interpret the signals and to correctly identify the various types of electrical events, including atrial beats (P-waves), ventricular beats (QRS complexes), and so on, which may occur. For example, it is common in demand pacemakers for various timing intervals to be started or stopped based upon detection of ventricular activity. Thus, a sensed ventricular event might inhibit a ventricular pacing output and initiate a base rate timer, a V-A escape interval timer, and an upper rate limit timer, while a sensed atrial event might inhibit an atrial pacing output and initiate an A-V delay interval timer. Operation of the pacemaker then depends upon whether certain expected events occur, and, if so, when such events occur in relation to the various time intervals established by the pacemaker.

While certain types of EGM events may be quite readily detected with a fair degree of certainty, there are certain other types of EGM events which are susceptible to being misinterpreted, misidentified (i.e., a false positive indication), or undetected (i.e., a false negative indication). As manifested in an EGM signal, viewed, for example, on a cathode ray tube or paper strip chart, one event may have only very subtle morphological differences from another, making discrimination and identification of either of the events quite difficult. The misidentification of, or inability to detect specific types of EGM events can have such undesirable consequences as preventing a therapeutic device from properly treating the heart, or improperly allowing the device to deliver a therapy when none is actually needed.

The ability to distinguish different morphologies would be useful in a number different situations, such as when it is necessary to discriminate between normal (antegrade) and abnormal (retrograde) activation of the atria. Such ability would be useful in preventing pacemaker mediated tachycardia (PMT), in which retrograde P waves or far-field R-waves cause continuous A-V sequential pacing at a high rate. At the present time, PMT is typically prevented by programming a prolonged post-ventricular atrial refractory period (PVARP) so that the retrograde P wave or far-field R-wave is not "seen" by the atrial channel; however, this limits the upper tracking rate of the pacemaker. Alternatively, various algorithms have been developed to terminate PMT once it is established. The ability to distinguish antegrade from retrograde P waves or far-field R-waves would be a far better solution to the problem of PMT. In this situation, retrograde P waves or far-field R-waves would be ignored by the pacemaker, abolishing the potential for PMT.

Another situation in which the ability to distinguish between the subtly different morphologies of certain types of EGM events is when it is necessary to discriminate between normal ventricular activation and abnormal ventricular activation. This would be useful in premature ventricular contraction (PVC) detection as well as detection of ventricular arrhythmias, such as ventricular tachycardia. Current generations of defibrillators use only a rate criteria to distinguish between normal beats and arrhythmias; the ability to distinguish between normal and abnormal EGM morphologies would be a significant improvement.

Various methods have been proposed in the prior art for distinguishing between different electrogram morphologies. In Wainwright et. al., "Ideal Atrial Lead Positioning to Detect Retrograde Atrial Depolarization by Digitization and Slope Analysis of the Atrial Electrogram ", PACE, 7:1152–1158, (1984), for example, there is proposed a digital system for examining changes in slew rates of the atrial EGM signals recorded from the right atrial appendage, high right atrium, and low right atrium, in order to distinguish antegrade from retrograde P waves. However, the signal processing capabilities described by Wainwright appear to be beyond that currently available in implantable devices.

Davies et. al., "Detection of Pathological Tachycardia by Analysis of Electrogram Morphology", PACE, 9:200–208, (1986), discussed the possibility of using the method described by Wainwright et al. to distinguish normal from abnormal ventricular activation. In Panizzo et. al., "Discrimination of Antegrade and Retrograde Atrial Depolarization by Electrogram Analysis", *American Heart Journal*, 112:780–786 (1986), measurement of EGM amplitudes and slew rates was proposed to distinguish antegrade from retrograde atrial activation. Panizzo et al. apparently concluded that combining a magnitude and slew rate threshold allowed discrimination of antegrade from retrograde P waves in 34 of 34 cases examined.

Timmis et. al., "Discrimination of Antegrade from Retrograde Atrial Electrograms for Physiologic Pacing", PACE, 11:130–140 (1988) discussed the examination of multiple EGM parameters, including peak-to-peak amplitude, duration, energy, maximum slew rate, mean slew rate, and polarity in the time domain, and maximum frequency, half-power frequency, Fourier amplitude peak, and frequency of peak in the frequency domain, and apparently concluded that no single parameter reliably distinguished antegrade from retrograde atrial activation, although the use of multiple parameters could be useful.

McAlister et. al., "Atrial Electrogram Analysis: Antegrade Versus Retrograde", PACE, 11: 1703–1707 (1988) suggested examination of morphology, slew rate, and amplitude criteria in discriminating antegrade from retrograde P waves, and seemed to indicate that morphology and slew rate did not increase the discriminatory power over amplitude alone. Lin et. al., "Identification of Ventricular Tachycardia Using Intracavitary Ventricular Electrograms: Analysis of Time and Frequency Domain Patterns", PACE, 11:1592–1606 proposed the use of sophisticated signal processing techniques, including correlation analysis and spectral analysis, in distinguishing ventricular tachycardia from sinus tachycardia, and suggested that the correlation waveform analysis is a reliable technique which requires significant data processing resources.

In view of the foregoing, it appears to the inventor that it would be desirable to provide morphologic analysis capability in an implantable device, in order to improve the device's ability to accurately detect and respond to various classes of EGM events.

SUMMARY OF THE INVENTION

The present invention relates to a method of distinguishing between EGM morphologies using phase space analysis. The phase space is an N-dimensional space with a variable x(t) plotted along one axis and $N-1$ of its derivatives, $(dx(t)/dt, d^2x(t)/dt^2$, etc.) plotted along mutually orthogonal axes. As x(t) and its derivatives vary in time, the point corresponding to the instantaneous values of x(t) and its derivatives can be plotted in phase space. Therefore, as the signal x(t) evolves in time, a curve (known as trajectory) is traced in phase space with time as a parameter. In the two-dimensional case where the relevant variables are x(t) and its first derivative dx(t)/dt, the phase space becomes a phase plane.

The advantage of phase space representations of a time-varying signal is that each of the axes (i.e., the signal and its derivatives) yields additional information about the signal; i.e., it is a way of increasing knowledge about what the signal is doing. Phase space representations can facilitate the observer's ability to detect subtle shifts in morphology of the signal, since both the signal as well as its derivatives are being examined for changes. In addition, periodic behavior is readily distinguished from non-periodic behavior by examining the patterns of the trajectories in phase space. As would be appreciated by those of ordinary skill in mathematics, the relevant measurements in the phase plane consist of: the magnitude, herein referred to as r(t), (i.e., distance of the point from the origin) of the trajectory at each point in time; and the angle, herein $\alpha(t)$, of the trajectory at each point in time.

Once the trajectory has been constructed and its magnitude and phase angle plots have been made, it is then possible to define a metric, i.e., a set of criteria, that can be applied in order to distinguish between the different trajectories of different signals. There are an infinite number of potential metrics than can be defined; some potential ones that could be derived by relatively simple hardware (i.e., hardware which could be included in an implantable device) include: determination of maximum value of the magnitude plot, determination of the angle of the trajectory at the maximum value of the magnitude, measurement of the area under the magnitude curve, measurement of the area under the phase angle curve, determination of the value of the largest derivative of the magnitude plot, or determination of the value of the largest derivative of the phase angle plot.

It is to be noted, however, in accordance with an important aspect of the present invention, that phase plane analysis is primarily a conceptual tool. Any practical realization of this method would not actually plot phase plane trajectories, but would use the concept in the design of the hardware or software to distinguish different signals.

In order to develop the concept of phase plane analysis of EGM signals, actual human atrial electrograms were obtained in a digitized format from a computer database. EGMs were obtained from two patients, LB and MM. Normal antegrade P waves were recorded for each patient. Retrograde P waves, caused by pacing the ventricle in the presence of retrograde (VA) conduction, were recorded for each patient. The signals analyzed were bipolar EGMs. The morphologies of the antegrade and retrograde P waves were quite different for patient MM and quite similar for patient LB, allowing a fair analysis of the technique.

Based upon these experimental results, the inventor has determined that there are numerous ways to distinguish antegrade from retrograde atrial EGM signals using phase plane representations. Possible metrics include: the number of complete circles around the origin while the magnitude exceeds a certain threshold, the angle of the maximum magnitude vector, or the mean value of the angle while the magnitude exceeds a certain threshold.

In accordance with one feature of the present invention, therefore, an apparatus is provided for analyzing EGM signals in the phase plane, and to generate signals representative of certain features of the phase plane representation of the EGM signals. In accordance with another feature of the present invention, the phase plane analysis circuitry is relatively simple, such that it may be readily implemented in an implantable device, such as a pacemaker, cardioverter, or defibrillator.

Another feature of the present invention is that the circuitry can be readily adapted to provide an indication of different characteristics of an EGM signal's trajectory in the phase plane, including, but not limited to, the number of circles made by the trajectory around the origin while the magnitude exceeds a predetermined threshold, the angle of the maximum magnitude vector of the trajectory, the mean value of the angle while the magnitude exceeds a predetermined threshold, and the areas under the magnitude and angle curves.

In accordance with another feature of the present invention, the information provided by the phase plane analysis circuitry provides an implantable device with a wide array of data from which specific types of events may be rendered distinguishable. In a preferred embodiment of the invention, circuitry is provided for deriving a plurality of phase plane parameters reflecting certain characteristics of a phase plane representation of a human EGM signal. In operation, the apparatus must first be "taught" or conditioned to recognize a particular event that is to be detected. This is accomplished by inducing an occurrence of the specified event in the patient, and applying the patient's EGM signals during the induced event to apparatus of the present invention. The phase plane parameters derived by the apparatus in response to the induced event EGM signals are then used to define a metric to be used as a basis for detection of future occurrences of the particular event. That is, various interrelationships among the phase plane parameters generated in response to the induced event are identified. Thereafter, when the patient's EGM signals are applied to the apparatus and such interrelationships are observed in the resulting phase plane parameters, these parameters can be taken as an indication that the specified event has occurred.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein:

FIGS. 1a, 1b, 1c, and 1d are plots of portions of human cardiac electrogram signals;

FIGS. 2a, 2b, 2c, and 2d are plots of the first derivative of the EGM signals from FIGS. 1a, 1b, 1c, and 1d, respectively;

FIG. 8b is a sample phase plot corresponding to the EGM signal and derivative from FIG. 8a; and FIG. 8c is a plot of the output signals produced by integrators in the circuit of FIG. 6 in response the signals from FIG. 8a;

FIG. 9b is a sample phase plot corresponding to the EGM signal and derivative from FIG. 9a; and FIG. 9c is a plot of the output signals produced by integrators in the circuit of FIG. 6 in response the signals from FIG. 9a;

FIG. 10b is a sample phase plot corresponding to the EGM signal and derivative from FIG. 10a; and FIG. 10c is a plot of the output signals produced by integrators in the circuit of FIG. 6 in response the signals from FIG. 10a;

FIG. 11b is a sample phase plot corresponding to the EGM signal and derivative from FIG. 11a; and FIG. 11c is a plot of the output signals produced by integrators in the circuit of FIG. 6 in response the signals from FIG. 11a;

DETAILED DESCRIPTION OF A SPECIFIC EMBODIMENT OF THE INVENTION

Figure 3A:
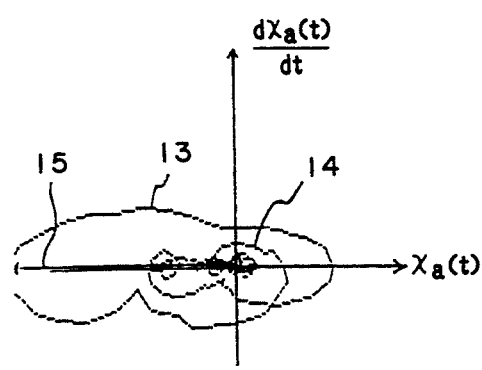
FIGS. 3a, 3b 3c, and 3d are phase plane plots derived from the plots from FIGS. 1a and 2a, and 1b, and 2b, 1cand 2c, and 1dand 2d, respectively.
Figure 3B:
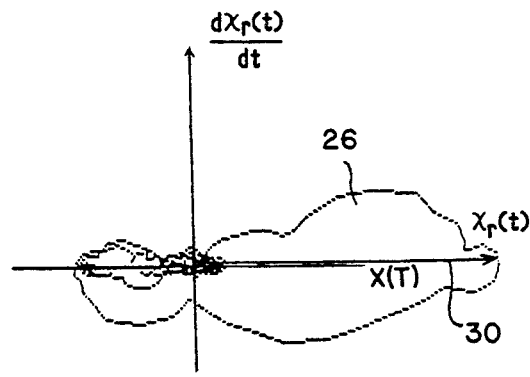
Figure 4A:
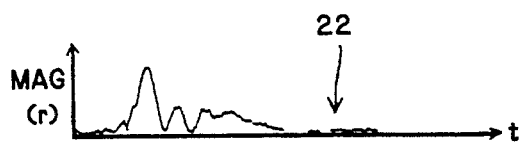
FIGS. 4a, 4b, 4c, and 4d are magnitude plots derived from the phase plane plots of FIGS. 3a, 3b, 3c, and 3d, respectively.
Figure 4B:
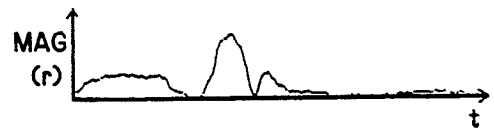

Referring first to FIGS. 1a, 1b, 2a, 2b, 3a, 3b, 4a, 4b, 5a, and 5b, there are shown a series of plots which will facilitate an understanding of the present invention. In FIGS. 1a and 1b, there is shown an EGM plot of $x_a(t)$ showing an antegrade atrial event (P-wave) within the dashed line designated as 10 and an EGM plot of $x_r(t)$ showing a retrograde P-wave within the dashed line designated as 12, respectively, from the aforementioned experimental subject MM. FIGS. 2a and 2b are plots of the respective first derivatives with respect to time, i.e., $dx_a(t)/dt$ and $dx_r(t)/dt$, of the curves $x_a(t)$ and $x_r(t)$ shown in FIGS. 1a and 1b. Next, in FIGS. 3a and 3b, there are shown phase plane plots of the signals from FIGS. 1a and 1b, respectively; that is, the phase plane plot of FIG. 3a corresponds to the graph of $x_a(t)$ from FIG. 1a (on the horizontal axis) versus $dx_a(t)/dt$ from FIG. 2a (on the vertical axis), while the phase plane plot of FIG. 3b corresponds to the graph of $x_r(t)$ from FIG. 1b versus $dx_r(t)/dt$ from FIG. 2b. FIGS. 4a and 4b are plots of the respective magnitude functions $r_a(t)$ and $r_r(t)$ versus time, where the magnitude function $r_a(t)$ corresponding to curves of FIGS. 1a and 2a is calculated as $$r_a(t) = \sqrt{(x_a(t))^2 + \left(\frac{dx_a(t)}{dt}\right)^2}$$

and the magnitude function $r_r(t)$ corresponding to the curves of FIGS. 1b and 2b is similarly calculated as $$r_r(t) = \sqrt{(x_r(t))^2 + \left(\frac{dx_r(t)}{dt}\right)^2}$$

Figure 5A:
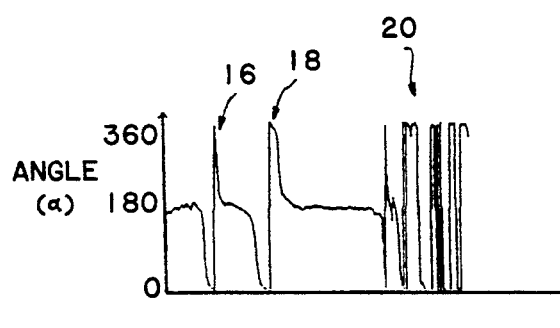
FIGS. 5a, 5b, 5c, and 5d are angle plots derived from the phase plane plots of FIGS. 3a, 3b, 3c, and 3d, respectively.
Figure 5B:
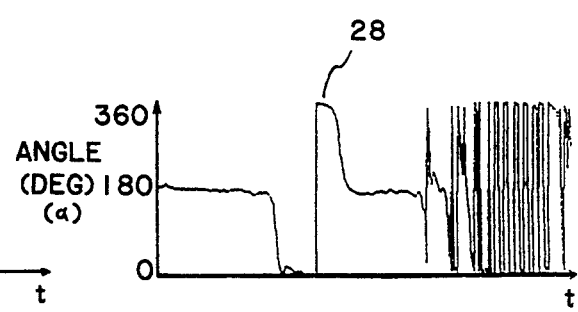

Finally, FIGS. 5a and 5b are plots of the respective angle functions $\alpha_a(t)$ and $\alpha_r(t)$ versus time, where $\alpha_a(t)$ is computed as $$\alpha_a(t) = \tan^{-1}\left(\frac{\left(\frac{dx_a(t)}{dt}\right)}{x_a(t)}\right)$$

and $\alpha_r(t)$ is similarly computed as $$\alpha_r(t) = \tan^{-1}\left(\frac{\left(\frac{dx_r(t)}{dt}\right)}{x_r(t)}\right)$$

where the positive x-axis is defined as 0° and the angle increases in the counterclockwise direction. The negative x-axis is 180° and the angle changes from 359° to 0° as it crosses the positive x-axis from below.

As shown in FIG. 3a, the phase plane plot of the antegrade P-wave designated within dashed line 10 starts just left of the origin, makes one large loops, designated as 13 in FIG. 3a, in the clockwise direction, returning to a point just left of the origin, then makes one small clockwise loop, designated as 14 in FIG. 3a. The angle of the maximum amplitude vector, designated as 15 in FIG. 3a, is 180°. This can also be seen with reference to a comparison of the plot of magnitude versus time shown in FIG. 4a with the plot of angle versus time shown in FIG. 5a; that is, when the magnitude is at a maximum, the angle is at 180°. The double transition of the angle plot through 360° (one designated as 16, one designated as 18 in FIG. 5a) signifies two complete rotations of the trajectory around the origin. It will be appreciated by those of ordinary skill in the art that the multiple transitions of the angle plot through 360° designated generally as 20 in FIG. 5a represent "jitter" of the trajectory of FIG. 1a back and forth across the x-axis; the very small magnitude corresponding to these multiple transitions (see the corresponding area denoted generally as 22 in the magnitude plot of FIG. 4a) suggests that this is merely "noise" which can be accounted for in practice through the use of a threshold comparator, as shall be hereinafter described in greater detail.

Referring now to the phase plane plot of FIG. 3b corresponding to the retrograde P-wave 12 in the region designated within dashed line 12, it will be noted that there is only one complete circling of the origin, designated as 26 in FIG. 3b, as can also be seen as the single transition 28 through 360° the plot of $\alpha_r(t)$ in FIG. 5b. Referring to FIGS. 4b and 5b together, the angle of the maximum magnitude vector 30 in FIG. 3b is 0° instead of 180° as in the antegrade case. The angle plot of FIG. 5b has a prolonged initial period at around 0°, in contrast to the antegrade case. The phase plane plot of FIG. 3b also has considerable low-level "jitter" of the angle around 0°, which can be accounted for with a threshold comparator as noted above.

From a comparison of the plots of FIGS. 1a, 2a, 3a, 4a, and 5a with FIGS. 1b, 2b, 3b, 4b, and 5b, it will be appreciated by those of ordinary skill in the art that a number of metrics for distinguishing between antegrade and retrograde P-waves may be considered, including the number of complete circles around the origin while the magnitude vector exceeds a predetermined threshold value, the angle of the maximum magnitude vector, or the mean value of the angle while the magnitude vector exceeds a predetermined threshold value.

In the particular case illustrated in FIGS. 1a–b, 2a–b, 3a–b, 4a–b, and 5a–b, it is apparent that one way of distinguishing between antegrade and retrograde P-waves in this patient is to compare the mean value of the magnitude vector in each quadrant of the phase plane. This may be accomplished, for example, by integrating the trajectory function separately for each quadrant of the phase plane. If the quadrants are identified as quadrant I ($r>0$; $0°<\alpha<90°$), quadrant II ($r>0$; $90°<\alpha<180°$), quadrant III ($r>0$; $180°<\alpha<270°$), and quadrant IV ($r>0$; $270°<\alpha<360°$), then for this particular patient, a metric for distinguishing between antegrade and retrograde P-waves could be expressed as follows: upon detection of an atrial event, if the integral of phase plane trajectory in quadrants II and III are greater than those for quadrants I and IV, this indicates an antegrade P-wave, while if the integral of the phase plane trajectory in quadrants I and IV are greater than those for quadrants II and III, this indicates a retrograde P-wave.

Figure 3C:
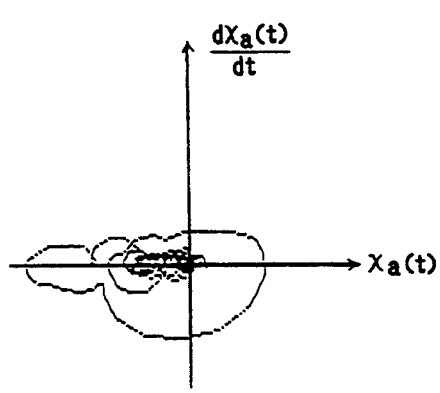
Figure 3D:
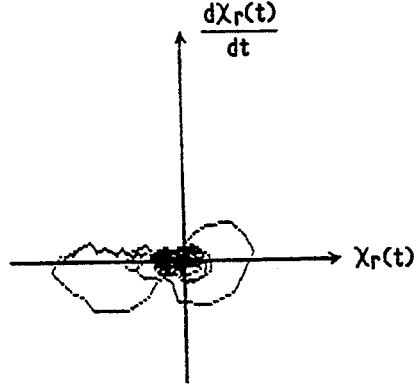
Figure 4C:
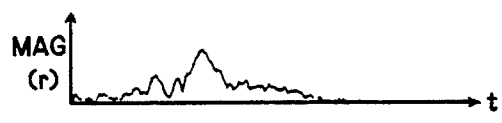
Figure 4D:
Figure 5C:
Figure 5D:
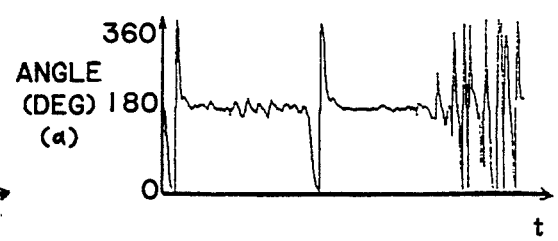

Similar data from experimental subject LB is depicted in FIGS. 1c–d, 2–d, 3c–d, 4c–d, and 5c–d. In particular, FIG. 1c is a plot of an antegrade P-wave (designated within dashed line 10') and FIG. 1d is a plot of a retrograde P-wave (designated within dashed line 12') as reflected in patient LB's EGM signal. FIGS. 2c and 2d are plots of the first derivative of the signals from FIGS. 1c and 1d, respectively. FIG. 3c is a plot of the phase plane trajectory obtained by plotting the function $x_a(t)$ from FIG. 1c against the function $dx_a(t)/dt$ from FIG. 2c; similarly, FIG. 3d is a plot of the phase plane trajectory obtained by plotting the function $x_r(t)$ from FIG. 1d against the function $dx_r(t)/dt$ from FIG. 2d. FIGS. 4c and 5c are the plots of the magnitude and angle components, respectively, of the phase plane trajectory of FIG. 3c, and FIGS. 4d and 5d are the plots of the magnitude and angle components, respectively, of the phase plane trajectory of FIG. 3d.

Examination of the respective phase plane trajectories resulting from antegrade and retrograde P-waves in patient LB suggests that the metric used for distinguishing between antegrade and retrograde P-waves in patient MM (described with reference to FIGS. 3a–b above) would not be appropriate for distinguishing between these two events in patient LB. Instead, analysis of the trajectories from FIGS. 3c and 3d shows that the area circumscribed by the trajectory of FIG. 3c for an antegrade P-wave is nearly one and one-half times greater than the area circumscribed by the trajectory of FIG. 3d for a retrograde P-wave. Thus, antegrade and retrograde P-waves could be distinguished based upon the sum of the integral of the phase trajectory in all four quadrants of the phase plane—if this sum exceeds a certain level, this could be taken as an indication of an antegrade P-wave, while if it does not, this could be taken as an indication of a retrograde P-wave.

Although the same metric may not be appropriate for detection of a particular cardiac event in every patient, it is contemplated that for a given patient, absent such additional complications such as ischemia or myocardial infarction, a given metric that is found suitable for a patient based upon observation of an induced event will continue to be a reliable and consistent indicator of the event in that patient. Thus, once a suitable metric has been defined for a patient, it will continue to be effective for that patient over a relatively long term.

Although a number of possible metrics have been noted herein, the present invention relates to a generalized, multi-function hardware arrangement which may generate many different signals and signal combinations reflecting various different aspects of the signal morphology. Thus, it is contemplated that the presently disclosed embodiment of the invention may have diverse applications and may be readily adapted to perform many different types of morphologic analyses. The present invention is not intended to be limited to a particular set of morphologic criteria. Furthermore, it is believed that different metrics may be more or less suitable for the purposes of discriminating between different kinds of events; that is, a metric which proves suitable for distinguishing antegrade from retrograde P-waves may not be as well-suited for distinguishing normal from premature ventricular contractions. It is contemplated, however, that the invention disclosed herein is suitable for many purposes, including not only atrial event discrimination and ventricular event discrimination, but also detecting ventricular tachycardia, ventricular fibrillation, atrial fibrillation, and so on.

Figure 6:
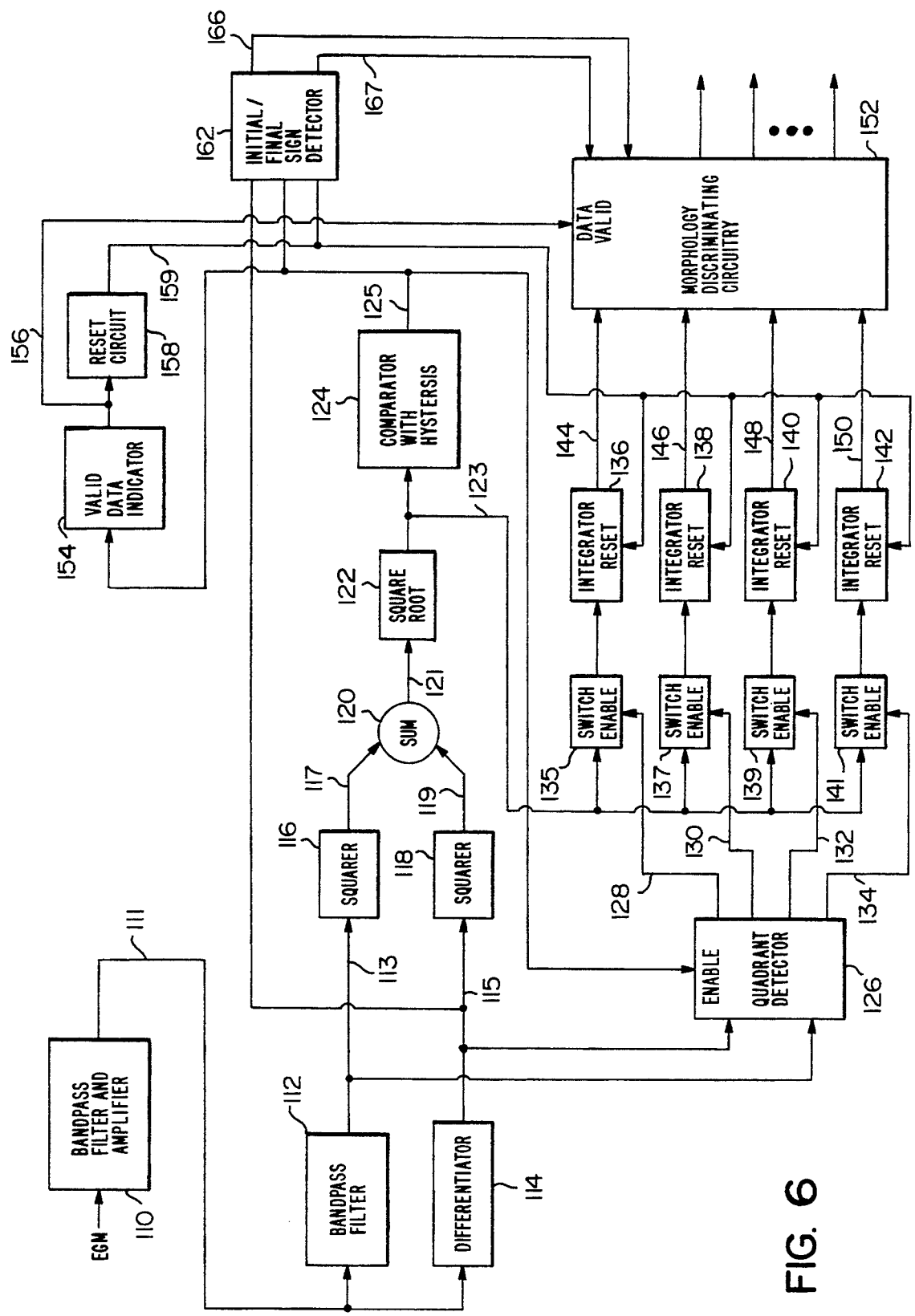
FIG. 6 is a block diagram of a phase plane analysis apparatus in accordance with one embodiment of the invention.

Turning now to FIG. 6, there is shown a block diagram of a phase-plane analysis circuit in accordance with one embodiment of the present invention. The circuit represented in FIG. 6 includes a bandpass filter and amplifier 110 which receives an EGM signal at its input. The bandpass filtered and amplified EGM signal (hereinafter referred to as x(t) is then conducted on line 111 to the respective inputs of a bandpass filter 112 and a differentiator 114. The filtered output signal from bandpass filter 112 is then applied, via line 113 to a first squaring circuit 116, while the differentiated output signal from differentiator 114 is conducted on line 115 to a second squaring circuit 118. Thus, if the signal on line 113 is denoted x(t), then the signal on line 115 is dx(t)/dt.

The output from squaring circuit 116, which corresponds to $x^2(t)$, is applied on line 117 to one input of a summing circuit 120, while the output from squaring circuit 118, which corresponds to $(dx(t)/dt)^2$, is applied to a second input of summing circuit 120. The output from summing circuit 120 therefore corresponds to $x^2(t)+(dx(t)/dt)^2$, and is applied on line 121 to a square root circuit 122. The positive output of square root circuit 122 thus corresponds to the magnitude vector r(t), where r(t) is given by the equation $$r(t) = +\sqrt{x(t)^2 + \left(\frac{dx(t)}{dt}\right)^2}$$

The r(t) signal on line 123 is applied to an input of a comparator with hysteresis 124, and also to an input of a series of integrator circuits 136, 138, 140, and 142. Comparator with hysteresis produces an output signal on line 125 which goes high when the magnitude signal r(t) on line 123 exceeds a predetermined threshold, and which goes low when r(t) falls to a predetermined level below the predetermined threshold. This hysteresis function performed by comparator 124 prevents the output signal from toggling on and off repeatedly should r(t) assume a value nearly equal to the predetermined threshold of comparator 124, as would be appreciated by those of ordinary skill in the art.

The signal on line 125 is applied to an enable input of a quadrant detector 126, which also receives as inputs the x(t) and dx(t)/dt signals on lines 113 and 115, respectively. Quadrant detector 126 produces four output signals, on lines 128, 130, 132, and 134. When quadrant detector 126 is enabled by the signal on line 125 at its enable input, the signal on line 128 is asserted when both of its inputs (i.e., x(t) and dx(t)/dt) are positive; i.e., r is in quadrant one. The signal on line 130, on the other hand, is asserted when detector 126 is enabled and when x(t) is negative but dx(t)/dt is positive; i.e., r is in quadrant two. The signal on line 132 is enabled when detector 126 is enabled, x(t) is negative and dx(t)/dt is negative; i.e., r is in quadrant three. Finally, the signal on line 134 is asserted when detector 126 is enabled and when x(t) is positive and dx(t)/dt is negative; i.e., r is in quadrant four. Thus, the signals on lines 128, 130, 132, and 134 function to identify which quadrant of the phase plane the phase plane representation of the EGM signal is currently in, so long as the representation of the EGM signal currently has a magnitude vector which exceeds the predetermined threshold set by comparator with hysteresis 124.

Thus, as will be appreciated by those of ordinary skill in the art, comparator with hysteresis 124 prevents the circuit of FIG. 6 from responding to the low-level "jitter" of phase-plane plots previously described above with reference to FIGS. 5a and 5b.

With continued reference to FIG. 6, the magnitude signal r(t) is applied to the inputs of the series of selectively actuable switches 135, 137, 139, and 141. Switches 135, 137, 139, and 141 are normally "open", so that signals at their respective inputs are not conducted to their respective outputs. However, output signal lines 128, 130, 132 and 134 from quadrant detector 126 are applied to ENABLE inputs of respective switches 135, 137, 139, and 141, so that when one of the quadrant detector outputs is asserted, a corresponding one of switches 135, 137, 139, and 141 will be "closed", allowing magnitude signal r(t) on line 123 to be conducted from the input of that switch through to its output, to be applied to a respective one of integrators 136, 138, 140 or 142.

At any given time, at most one of the quadrant-identifying signals will be asserted, so that at any given time, only one of the integrators 136, 138, 140, or 142 will have the magnitude signal r(t) applied thereto via a corresponding one of switches 135, 137, 139, and 141. Thus, the output of each integrator 136, 138, 140, and 142 is a value representing the amount and duration of time that the magnitude signal r(t) exceeds the predetermined threshold value of comparator 124 in a particular quadrant and is proportional to the area within the trajectory in each respective quadrant.

As shown in FIG. 6, the output signal on line 125 from comparator 124 is, in addition to being applied to the ENABLE input of quadrant detector 126, also applied to the input of a valid data indicator circuit 154. Valid data indicator circuit is essentially a falling-edge triggered one-shot circuit which asserts an output signal on line 156 when comparator 124 deasserts its output signal on line 125. The data valid signal on line 156 is provided to morphology discriminating circuit 152 to indicate completion of a phase plane trajectory analysis (i.e., to indicate when a trajectory no longer exceeds the threshold value of comparator 124). In addition, the data valid signal on line 156 is applied to an input of a reset circuit 158. In response to an assertion of the data valid signal on line 156, reset circuit 158 waits for a predetermined time interval and then asserts an output signal on line 159 which is applied to a RESET input of integrators 136, 138, 140 and 142. The predetermined time interval corresponds to a data valid window during which time the output voltages from integrators 136, 138, 140 and 142 may be examined by discriminating circuit 152. After this time interval, reset circuit asserts the signal on line 159, thereby resetting the outputs of integrators 136, 138, 140, and 142 in preparation for analysis of another trajectory having sufficient magnitude to trigger comparator 124.

The circuit of FIG. 6 also includes a circuit 162 for identifying the initial and final signs of the derivative. Initial/final sign detector circuit 162 receives the signal on line 115 corresponding to dx(t)/dt. In addition, circuit 162 receives the enable signal conducted on line 125. When the enable signal on line 125 goes high, indicating that r(t) has exceeded the predetermined threshold of comparator 124, the initial sign (i.e., positive or negative) of dx(t)/dt is latched by circuit 162. Similarly, when the signal on line 125 goes low, the final signal of dx(t)/dt is latched by circuit 162. Signals representing the initial and final signs of dx(t)/dt are then conducted on output lines 166 and 167 to morphology discriminating circuit 152, where they may be incorporated into the metric for identifying a particular phase plane trajectory morphology.

Figure 7:
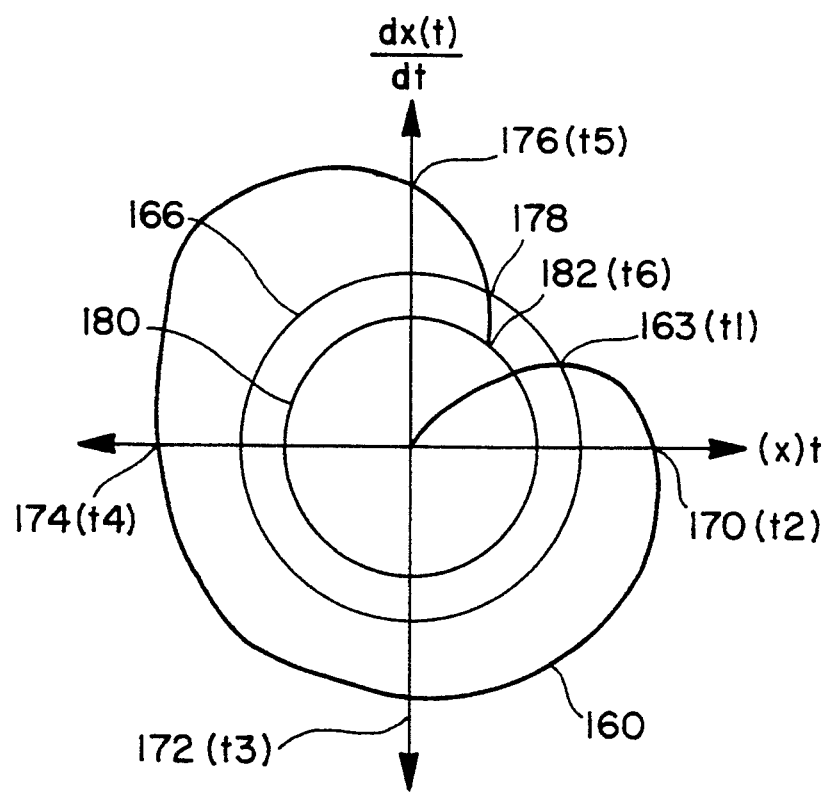
FIG. 7 is a sample phase plane trajectory plot.

Operation of the circuit represented in FIG. 6 will perhaps be better understood with reference to an example of a phase plane trajectory 160, shown in FIG. 7. It is to be understood that curve 160 in FIG. 7 is only an example of a phase plane trajectory, and is substantially simplified, for the purpose of illustration, as compared with signals derived from actual EGM inputs to the circuit of FIG. 6.

In FIG. 7, phase plane trajectory 160 begins, at a time $t_0$, at a point 162 ($t_0$) near the origin. As phase plane trajectory 160 travels outward from point 162 beginning at time $t_0$, its magnitude component r(t) increases. In FIG. 7, circle 166 represents the threshold of comparator 124, such that any signal having a magnitude less than that threshold will not cause the output from comparator 124 to become asserted. When the magnitude component r(t) of phase plane trajectory 160 is less than the threshold value of comparator 124, (i.e., when phase plane trajectory 160 is within circle 166 in FIG. 7), quadrant detector 126 is not enabled, and all switches 135, 137, 139, and 141 are open. Therefore, in this situation, integrators 136, 138, 140, and 142 integrate a zero value; therefore, the outputs from integrators 136, 138, 140, and 142 would remain unchanged. It is to be understood that initially, the integrators' output values are all zero, due to the above-described operation of reset circuit 158.

At a time $t_1$, the magnitude component r(t) of phase plane trajectory 160 crosses threshold circuit 166, at a point designated as 163. At time $t_1$, therefore, comparator 124 will assert its output on line 125, thereby enabling quadrant detector 126. Since both x(t) and dx(t)/dt are positive at time $t_1$, quadrant detector 126 will assert the signal on line 128 to close the switch 135 corresponding to positive x(t) and positive dx(t)/dt. As a result, the magnitude signal r(t) will be conducted to the input of integrator 136, which will perform an integration of the r(t) signal. This is reflected in an increase in the output signal from integrator 136 on line 144 in the interval between times $t_1$ and $t_2$.

At point 170 (time $t_2$), phase plane trajectory 160 crosses the horizontal axis, with dx(t)/dt now being negative. Since r(t) still exceeds threshold line 168, quadrant detector 126 remains enabled, but asserts the signal on line 134 instead of that on line 128, since dx(t)/dt is now negative. Therefore, at time $t_2$ switch 141 will be closed and switch 128 will be re-opened. Thus, integrator 136 resumes integration of a zero value while integrator 142 begins integrating the magnitude signal r(t) in the time interval between times $t_2$ and $t_3$.

At point 172 (time $t_3$) in FIG. 7, phase plane trajectory 160 crosses the vertical axis, so that both x(t) and dx(t)/dt are now negative. This causes quadrant detector to assert the signal on line 132 instead of that on line 130, closing switch 139 and opening switch 141. Thus, at time $t_3$ integrator 140 will begin integrating the magnitude signal r(t) and integrator 142 will cease doing so.

At point 174 (time $t_4$) in FIG. 7, trajectory 160 again crosses the horizontal axis, so that dx(t)/dt is now positive and x(t) remains negative. Thus, at time $t_4$, integrator 138 will begin integrating the magnitude function r(t) applied thereto via switch 137, and integrator 140 will cease doing so.

At point 176 (time $t_5$) in FIG. 7, trajectory 160 crosses the vertical axis so that both x(t) and dx(t)/dt are once again both positive. As before, this will result in application of the magnitude signal r(t) to integrator 136 via switch 135, resulting in a second interval of increase in the output from integrator 136.

At some time after time $t_5$, trajectory 160 turns inward toward the origin, crossing into circle 166 at point 178, and crossing into circle 180 at a point 182 (time $t_6$). Circle 180 represents a second threshold value corresponding to the voltage at which comparator 124 will deassert its output signal on line 125. The threshold value represented by circle 180 is less than that represented by circle 166; this difference arises due to the hysteresis of comparator 124. As would be appreciated by those of ordinary skill in the circuit art, the fact that comparator 124 has a hysteresis function means that although a signal having a magnitude greater than that represented by circle 166 in FIG. 7 is required before comparator 124 will assert its output, the signal must fall below the level represented by circle 180 before comparator 124 will deassert its output.

At time $t_6$, when trajectory 160 crosses threshold 180 and magnitude function r(t) crosses threshold 184, comparator 124 will deassert its output on line 125, thereby disabling quadrant detector 126. Thus, none of switches 135, 137, 139, and 141 will be closed, and the output voltages from integrators 136, 138, 140, and 142 will thereafter remain unchanged.

In addition, when comparator 124 deasserts the output signal on line 125, data valid detector asserts its output signal on line 156, indicating to discriminating circuit 152 that the output values from integrators 136, 138, 140 and 142 may be read. Discriminating circuit 152 must read the integrator output values during the time window defined by the time delay of reset circuit. After this time delay, reset circuit will issue its reset signal on line 159, restoring the output values of integrators 136, 138, 140 and 142 to zero values. Thus, the circuit of FIG. 6 is put into a state of readiness for a subsequent input signal having a phase plane trajectory with magnitude sufficient to trigger comparator 124.

Figure 8A:
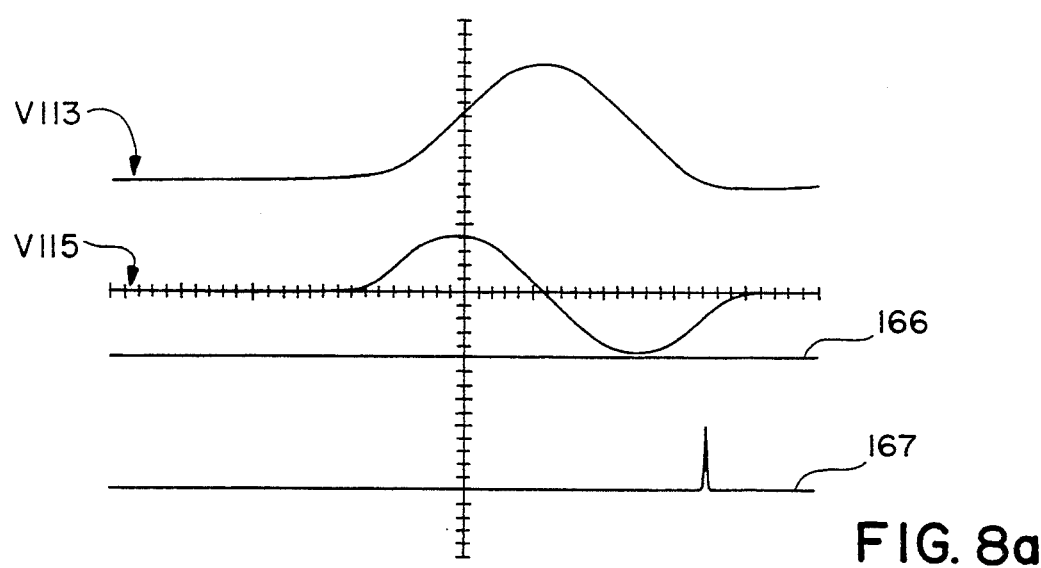
FIG. 8a is a plot of a sample filtered EGM signal and its derivative.

As previously noted, the phase plane trajectory of FIG. 7 is a hypothetical one that has been provided only for the purposes of describing the operation of the circuit of FIG. 6. In FIGS. 8a-c through 12a-c, there are shown various plots of actual signals applied to the circuitry of FIG. 6. As shown in FIG. 6, the EGM input signal is applied to the EGM input of bandpass filter and amplifier 110. The output of filter/amplifier 110 is then applied to the respective inputs of filter 112 and differentiator 114. If the output of filter 112 is designated as x(t) then the output of differentiator 114 is dx(t)/dt, the first derivative of x(t). In FIG. 8a, a first waveform V113 corresponds to the bandpass filtered EGM signal x(t) that is conducted on line 113 in the circuit of FIG. 6. A second waveform V115 in FIG. 7a represents the differentiated EGM signal dx(t)/dt that is conducted on line 115 in the circuit of FIG. 6.

Figure 8B:
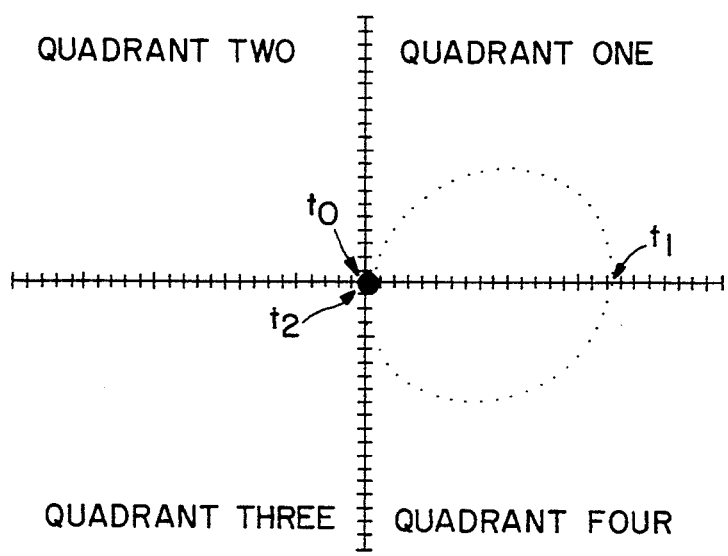
Figure 8C:
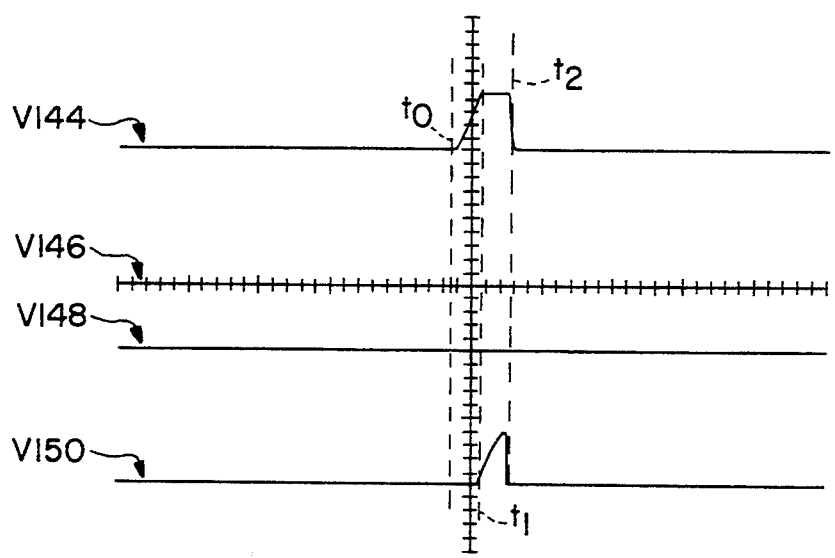

In FIG. 8b, there is shown a phase-plane plot of the waveforms V113 and V115, with waveform V113 being plotted along the X-axis and waveform V115 being plotted on the Y-axis. In FIG. 8c, there are shown the waveforms of the outputs of integrators 136, 138, 140, and 142, which outputs are conducted on lines 144, 146, 148, and 150, respectively. In FIG. 8c, the signal conducted on line 144 is designated as V144, the signal on line 146 is designated as V146, and so on.

As would be appreciated by those of ordinary skill in the art, the waveform V144 in FIG. 8c represents the amount and duration of time that the phase plane trajectory of FIG. 8b exceeds the predetermined threshold value of comparator 124 in quadrant one of the phase plane, and is proportional to the area within the trajectory of FIG. 8b in quadrant one. Notice from FIGS. 8b and 8c that waveform V144 increases during the interval from time $t_0$ to $t_1$, while the phase plane trajectory of FIG. 8b is in quadrant 1. Similarly, waveform V150 represents the amount and duration of time that the phase plane trajectory of FIG. 8b exceeds the predetermined threshold value of comparator 124 in quadrant four of the phase plane, and is proportional to the area within the trajectory in quadrant four. Thus, waveform V150 increases during the interval from time $t_1$ to $t_2$.

It should be noted that waveforms V146 and V148 in FIG. 8c stay at a zero value, since the trajectory of FIG. 8b does not enter quadrants two or three.

Figure 9A:
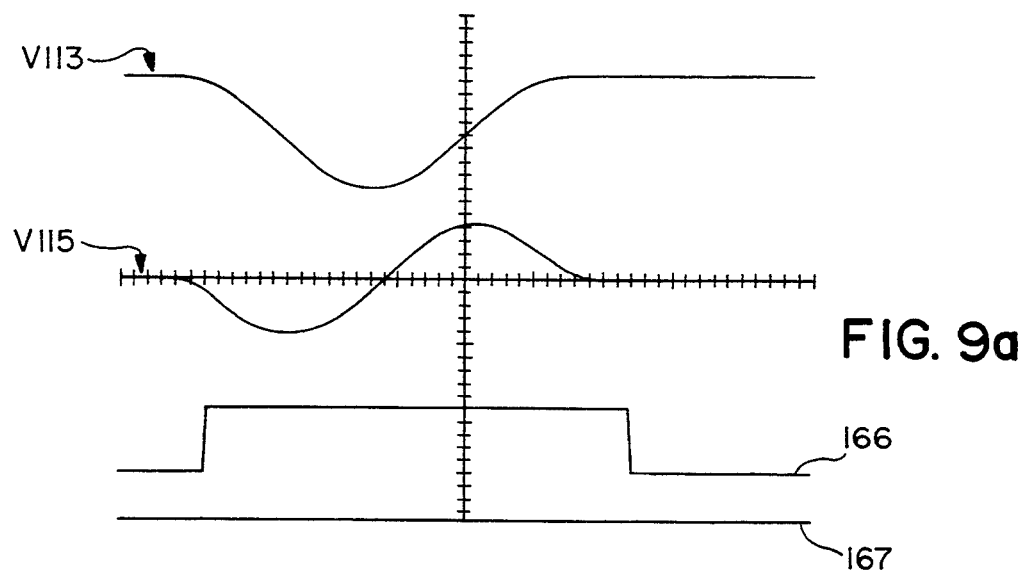
FIG. 9a is a plot of a sample filtered EGM signal and its derivative.
Figure 9B:
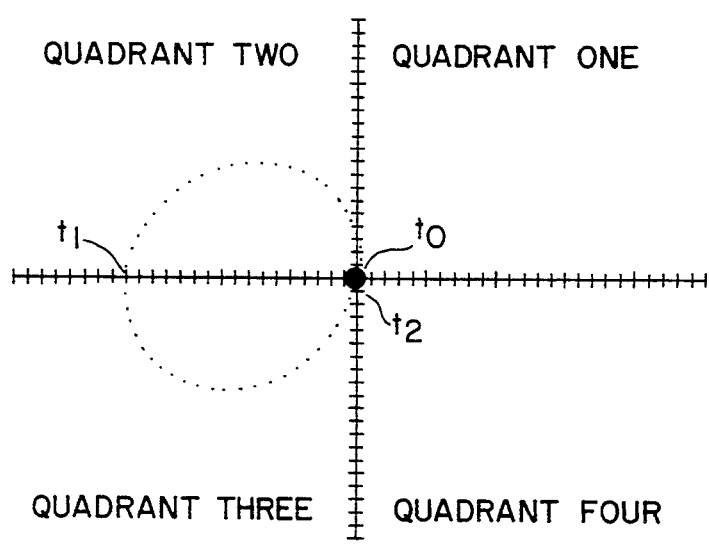
Figure 9C:
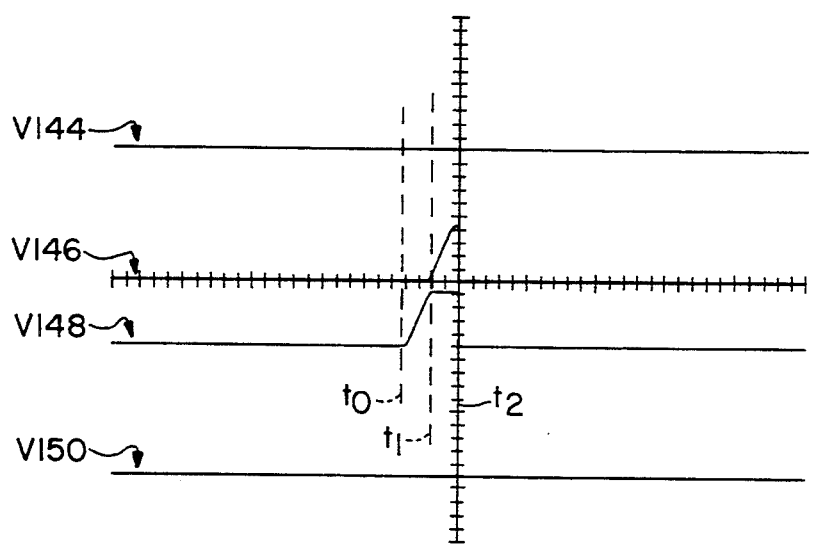
Figure 10A:
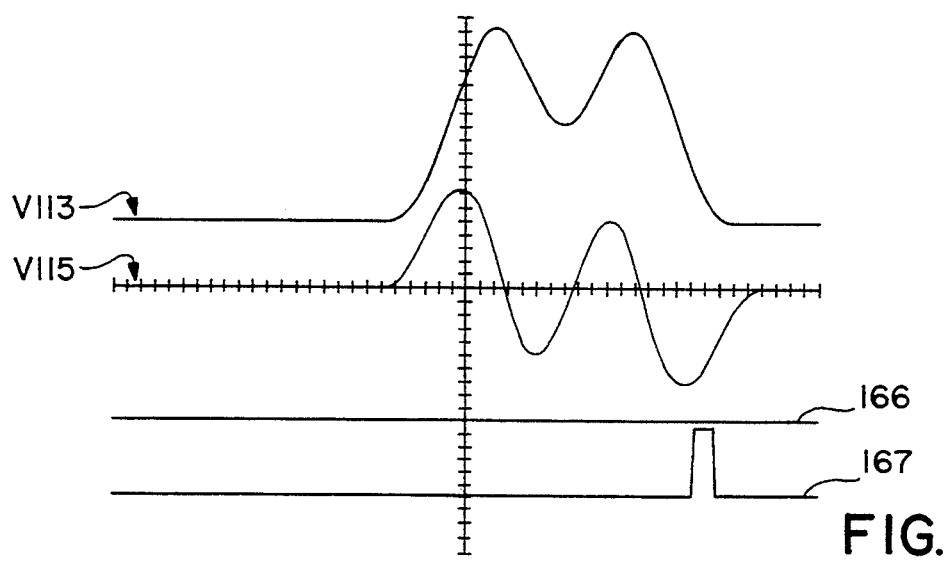
FIG. 10a is a plot of a sample filtered EGM signal and its derivative.
Figure 10B:
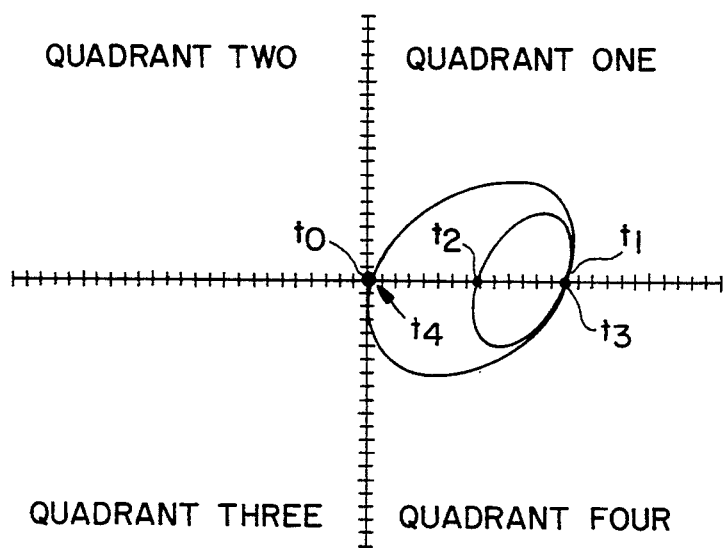
Figure 10C:
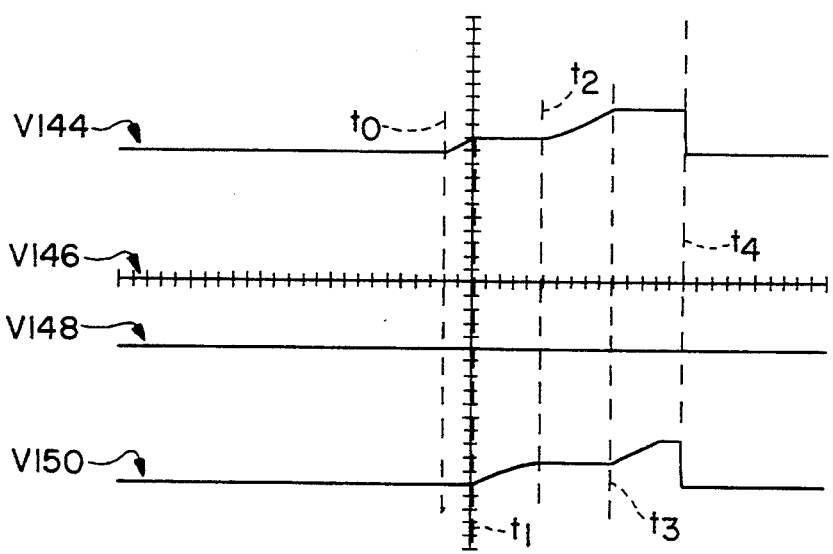
Figure 11A:
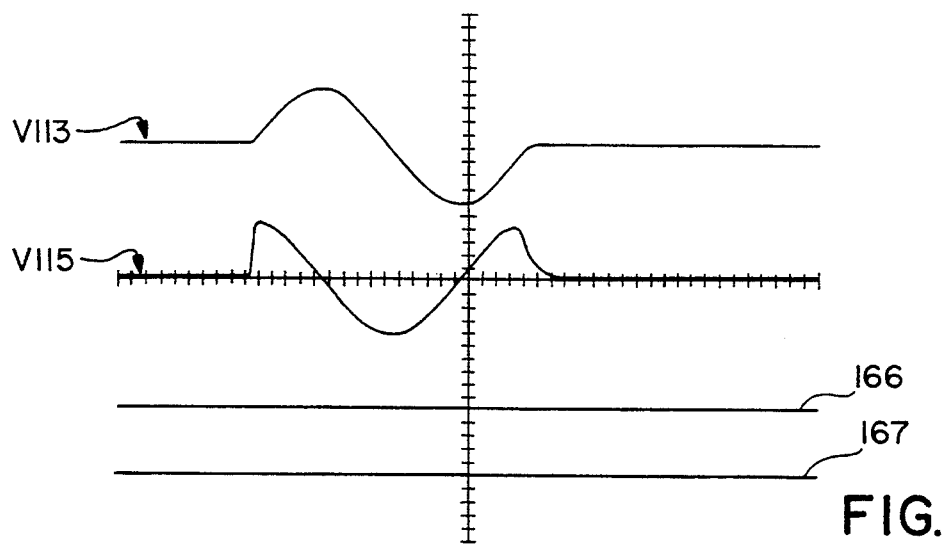
FIG. 11a is a plot of a sample filtered EGM signal and its derivative.
Figure 11B:
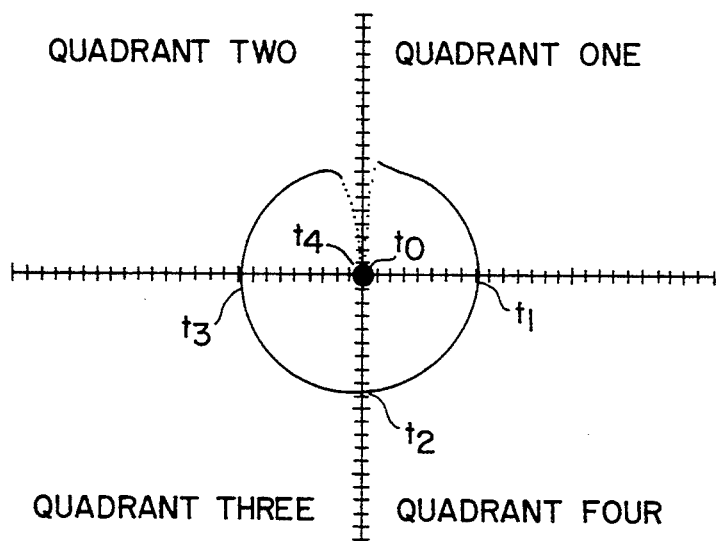
Figure 11C:
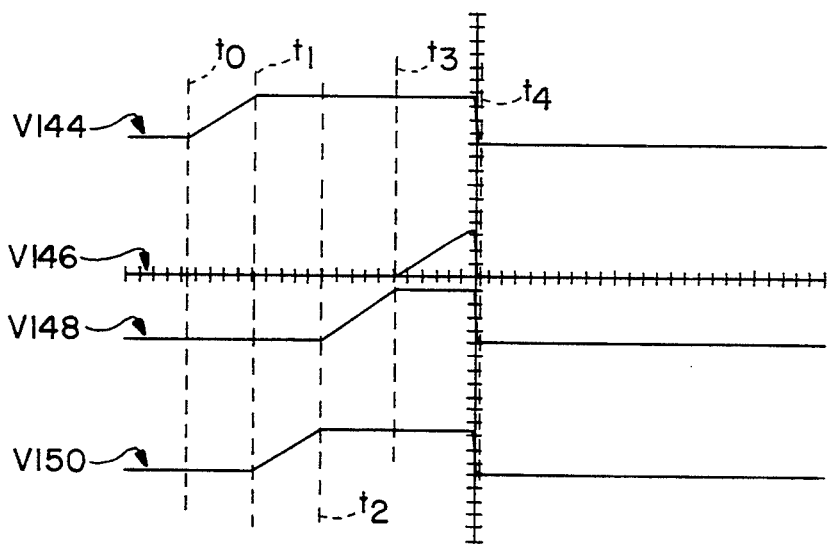

FIGS. 9a, 9b, and 9c are, like FIGS. 8a, 8b, and 8c, plots showing an filtered input signal (V113 in FIG. 9a) that appears on line 113 in the circuit of FIG. 6, its derivative (V115 in FIG. 9a) that appears on line 115, the phase plane trajectory obtained by plotting V113 versus V115 (FIG. 9b), and the output waveforms from integrators 136, 138, 140, and 142 (waveforms V144, V146, V148, and V150 in FIG. 9c).

Likewise, FIGS. 10a–c and 11a–c are sets of plots showing a filtered input signal (V113) and its derivative (V115) (FIGS. 10a and 11a) the corresponding phase plane plot (FIGS. 10b and 11b) and the integrator output waveforms (V144, V146, V148, and V150) (FIGS. 10c and 11c), for different input EGM signals.

When discriminating circuit reads the integrator output values, it is thereby provided with information about the morphology of the incoming EGM signal which would not be apparent from analysis of the signal alone, without the phase plane analysis which takes into account the signal and at least one of its derivatives. In accordance with an important feature of the present invention, it is contemplated that in addition to the integrator output values, discriminating circuit may also be provided with other signals that are produced within the circuit shown in FIG. 6, such as the magnitude signal r(t) on line 123, the signals x(t) and dx(t)/dt on lines 113 and 115, respectively, or the incoming EGM signal itself. It is for the sake of clarity only that connections for directly providing such additional signals to discriminating circuit 152 are not shown in FIG. 6.

It is further contemplated that additional derivatives of x(t) may be produced in the circuit of FIG. 6, by merely cascading differentiator circuits identical to 114 in FIG. 6 in a manner which would be readily apparent to one of ordinary skill in the art. Such additional derivative signals could then be used in more comprehensive discriminating metrics which might be realized in discriminating circuit 152.

Also, with regard to the magnitude threshold established by comparator 124, which threshold has a circular representation in the phase plane, it is contemplated that variations on this threshold function could be implemented. For example, comparators might be interposed along lines 113 and 115 to activate switches 135, 137, 139, and 141 whenever x(t) is within predetermined upper and lower limits at the same time that dx(t)/dt is within predetermined upper and lower limits. Such an arrangement would result in a threshold which would be represented in the phase plane as a rectangular region, rather than circular one. In any case, it is believed to be preferable for the threshold to be capable of being varied so that in a practical application of the invention the circuit may be customized according to an individual patient's parameters.

It is further contemplated that simple circuitry that could be readily provided by those of ordinary skill in the circuit art might be applied to the output of quadrant detector 126, so that, for example, the number of complete revolutions of the phase plane trajectory of a signal might be monitored and counted, such information also being applied to discriminating circuitry 152 to be used in conjunction with a particular metric.

Since, as described above, the appropriate metric for identifying a particular cardiac event may differ from one patient to the next, an important step in the utilization of an apparatus in accordance with the present invention is the conditioning of discrimination circuitry 152 to recognize certain distinguishing features of the phase plane signals specific to an individual patient. It is contemplated that such conditioning may be accomplished by first inducing in the patient the event to be detected in accordance with the present invention, and then evaluating features and characteristics of the resultant phase plane trajectory. Having done so, a metric may be selected that is appropriate for the patient. Circuitry for allowing programmability or selection of the metric to be used for a given patient may include RAM or ROM memory for storing digital representations of analog values against which the integrator output signals may be compared; or analog reference voltage storage devices; or hard-wired analog and digital circuitry.

For example, in the case of experimental subject MM whose trajectories for antegrade and retrograde P-waves were depicted in FIGS. 3a and 3b above, it was determined that a comparison of the integrals from quadrants II and III with those from quadrants I and IV would served to distinguish antegrade from retrograde P-waves. It is believed that it would be a matter of routine for those of ordinary skill in the art to implement a comparison of such values in discrimination circuitry 152. For example, it would be a simple matter to apply the integrator signals from integrators 136, 138, 140, and 142 to voltage comparators in order to produce an ANTEGRADE output signal from circuit 152 when the integrals from quadrants II and III exceed those from quadrants I and IV, and a RETROGRADE output signal from circuit 152 when the opposite relationship exists.

In the case of experimental subject LB whose phase plane trajectories for antegrade and retrograde P-waves were depicted in FIGS. 3c and 3d, it would be a matter of routine to sum the outputs signals from integrators 136, 138, 140, and 142, and to then produce an ANTEGRADE output signal when this sum exceeds a predetermined level and a RETROGRADE output signal when this sum does not exceed a predetermined level.

It is further believed that it would be a matter of routine for those of ordinary skill in the art to provide general, multi-function circuitry 152 which would be programmably controllable to perform various types of comparisons, summations, or other basic operations on the integrator output signals in order to generate signals reflecting various features of the phase plane trajectory, as appropriate for a given patient.

Although the metric appropriate for identifying a particular cardiac event in one patient may not be appropriate for another, it is believed that for a given patient, once an appropriate metric has been defined, it should provide a reliable and consistent basis for discrimination between different events over a relatively long period of time, unless a condition that might change the morphology, such as ischemia, myocardial infarction, or the like arises.

Figure 12:
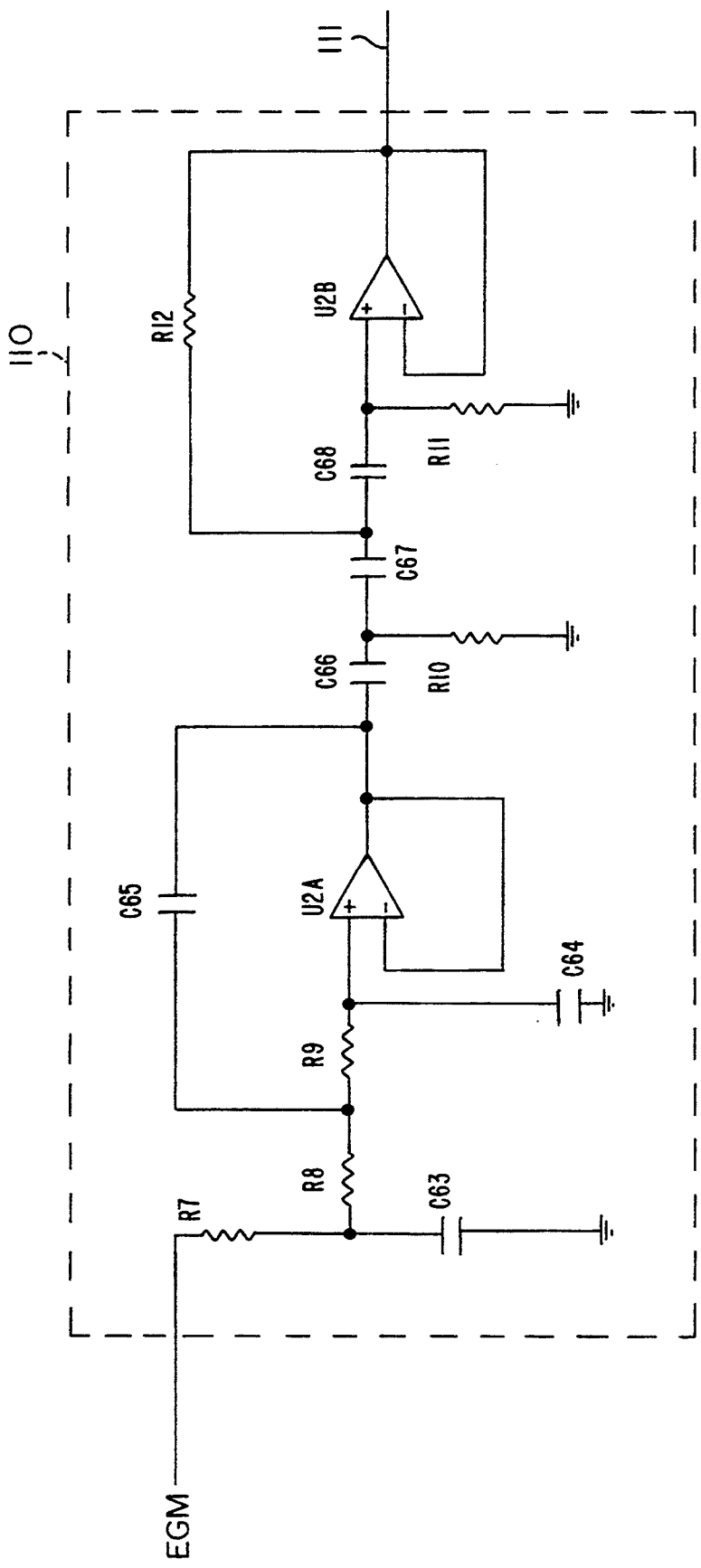
FIG. 12 is a schematic diagram of the bandpass filter and amplifier from the block diagram of FIG. 6.

Turning now to FIGS. 12 through 19, there are shown more detailed schematic diagrams of the circuitry represented in block form in FIG. 6. In FIGS. 12 through 19, it is to be understood that corresponding components in the block diagram of FIG. 6 have retained identical reference numeral designations. For example, the specific circuitry embodying bandpass filter and amplifier 110 in the block diagram of FIG. 6 is similarly designated within a dashed line 110 in FIG. 12. Also, it is to be understood that a certain component shown on one of the schematics of FIGS. 12 through 19 may be connected to a component shown on a different one of those schematics. For example, bandpass filter 110 in FIG. 12 is coupled, via conductor 111 to the inputs of bandpass filter 112 and differentiator 114 shown in FIG. 13. It will be assumed therefore that conductor 111 in FIG. 12 is connected to and identical to conductor 111 in FIG. 13.

The types and values of each of the components shown in FIGS. 12 through 19 are set forth in the following Table 1. Each of the components are commercially available, off-the-shelf parts; it is contemplated, however, that particularly in the context of an implantable device, the present invention would advantageously be practiced with a custom integrated circuit, or the like.

TABLE 1

| Item | Quantity | Reference | Part |
|---|---|---|---|
| 1 | 1 | C84 | 1.5 nf |
| 2 | 2 | C1 | 68 µf |
|   |   | C2 | 68 µf |
| 3 | 61 | C3 | 0.1 µf |
|   |   | C4 | 0.1 µf |
|   |   | C5 | 0.1 µf |
|   |   | C6 | 0.1 µf |
|   |   | C7 | 0.1 µf |
|   |   | C8 | 0.1 µf |
|   |   | C9 | 0.1 µf |
|   |   | C10 | 0.1 µf |
|   |   | C11 | 0.1 µf |
|   |   | C12 | 0.1 µf |
|   |   | C13 | 0.1 µf |
|   |   | C14 | 0.1 µf |
|   |   | C15 | 0.1 µf |
|   |   | C16 | 0.1 µf |
|   |   | C17 | 0.1 µf |
|   |   | C18 | 0.1 µf |
|   |   | C19 | 0.1 µf |
|   |   | C20 | 0.1 µf |
|   |   | C21 | 0.1 µf |
|   |   | C22 | 0.1 µf |
|   |   | C23 | 0.1 µf |
|   |   | C24 | 0.1 µf |
|   |   | C25 | 0.1 µf |
|   |   | C26 | 0.1 µf |
|   |   | C27 | 0.1 µf |
|   |   | C28 | 0.1 µf |
|   |   | C29 | 0.1 µf |
|   |   | C30 | 0.1 µf |
|   |   | C31 | 0.1 µf |
|   |   | C32 | 0.1 µf |
|   |   | C33 | 0.1 µf |
|   |   | C34 | 0.1 µf |
|   |   | C35 | 0.1 µf |
|   |   | C36 | 0.1 µf |
|   |   | C37 | 0.1 µf |
|   |   | C38 | 0.1 µf |
|   |   | C39 | 0.1 µf |
|   |   | C40 | 0.1 µf |
|   |   | C41 | 0.1 µf |
|   |   | C42 | 0.1 µf |

TABLE 1-continued

| Item | Quantity | Reference | Part |
|---|---|---|---|
|   |   | C43 | 0.1 µf |
|   |   | C44 | 0.1 µf |
|   |   | C45 | 0.1 µf |
|   |   | C46 | 0.1 µf |
|   |   | C47 | 0.1 µf |
|   |   | C48 | 0.1 µf |
|   |   | C49 | 0.1 µf |
|   |   | C50 | 0.1 µf |
|   |   | C51 | 0.1 µf |
|   |   | C52 | 0.1 µf |
|   |   | C53 | 0.1 µf |
|   |   | C54 | 0.1 µf |
|   |   | C55 | 0.1 µf |
|   |   | C56 | 0.1 µf |
|   |   | C57 | 0.1 µf |
|   |   | C58 | 0.1 µf |
|   |   | C59 | 0.1 µf |
|   |   | C60 | 0.1 µf |
|   |   | C61 | 0.1 µf |
|   |   | C62 | 0.1 µf |
|   |   | C80 | 0.1 µf |
| 4 | 2 | C63 | 0.1 µf |
|   |   | C71 | 0.1 µf |
| 5 | 1 | C64 | 0.33 µf |
| 6 | 1 | C65 | 0.38 µf |
| 7 | 3 | C66 | 3.19 µf |
|   |   | C67 | 3.19 µf |
|   |   | C68 | 3.19 µf |
| 8 | 1 | C69 | 33 nf |
| 9 | 1 | C70 | 10 µf |
| 10 | 1 | C72 | 0.01 µf |
| 11 | 1 | C73 | 30 pf |
| 12 | 1 | C75 | 100 µf |
| 13 | 4 | C76 | 1 µf |
|   |   | C77 | 1 µf |
|   |   | C78 | 1 µf |
|   |   | C79 | 1 µf |
| 14 | 1 | C82 | 0.01 |
| 15 | 1 | C83 | 22 nf |
| 16 | 1 | D1 | 1N4148 |
| 19 | 1 | R1 | 100 MΩ |
| 20 | 1 | R2 | 1 MΩ |
| 21 | 13 | R3 | 10 KΩ |
|   |   | R6 | 10 KΩ |
|   |   | R7 | 10 KΩ |
|   |   | R8 | 10 KΩ |
|   |   | R17 | 10 KΩ |
|   |   | R22 | 10 KΩ |
|   |   | R31 | 10 KΩ |
|   |   | R40 | 10 KΩ |
|   |   | R41 | 10 KΩ |
|   |   | R42 | 10 KΩ |
|   |   | R43 | 10 KΩ |
|   |   | R70 | 10 KΩ |
| 22 | 2 | R4 | 500 KΩ |
|   |   | R37 | 500 KΩ |
| 23 | 1 | R5 | 5 KΩ |
| 24 | 1 | R10 | 760 KΩ |
| 25 | 1 | R11 | 1.03 MΩ |
| 26 | 1 | R12 | 208 KΩ |
| 27 | 1 | R13 | 8 KΩ |
| 28 | 1 | R14 | 24 KΩ |
| 29 | 1 | R15 | 318 KΩ |
| 30 | 1 | R16 | 640 KΩ |
| 31 | 1 | R18 | 115 KΩ |
| 32 | 1 | R19 | 7.96 KΩ |
| 33 | 1 | R20 | 79.6 KΩ |
| 34 | 1 | R21 | 7.5 KΩ |
| 35 | 1 | R23 | 9.5 KΩ |
| 36 | 1 | R24 | 1.5 MΩ |
| 37 | 6 | R25 | 100 KΩ |
|   |   | R26 | 100 KΩ |
|   |   | R27 | 100 KΩ |
|   |   | R28 | 100 KΩ |
|   |   | R36 | 100 KΩ |
|   |   | R69 | 100 KΩ |
| 38 | 1 | R29 | 2.2 KΩ |
| 39 | 1 | R30 | 47 KΩ |
| 40 | 4 | R32 | 20 KΩ |
|   |   | R33 | 20 KΩ |
|   |   | R34 | 20 KΩ |

TABLE 1-continued

| Item | Quantity | Reference | Part |
|---|---|---|---|
|  |  | R39 | 20 KΩ |
| 41 | 2 | R35 | 1 KΩ |
|  |  | R38 | 1 KΩ |
| 42 | 4 | R44 | 56 KΩ |
|  |  | R45 | 56 KΩ |
|  |  | R46 | 56 KΩ |
|  |  | R47 | 56 KΩ |
| 43 | 4 | R56 | 50 KΩ |
|  |  | R57 | 50 KΩ |
|  |  | R58 | 50 KΩ |
|  |  | R59 | 50 KΩ |
| 44 | 1 | R67 | 110 kΩ |
| 45 | 1 | SW1 | 1RSW10 |
| 46 | 1 | U1 | LH0036 |
| 47 | 2 | U2 | LM324 |
|  |  | U3 | LM324 |
| 48 | 1 | U4 | LM308 |
| 49 | 3 | U5 | AD532 |
|  |  | U6 | AD532 |
|  |  | U7 | AD532 |
| 50 | 10 | U8 | LM311 |
|  |  | U9 | LM311 |
|  |  | U10 | LM311 |
|  |  | U11 | LM311 |
|  |  | U12 | LM311 |
|  |  | U13 | LM311 |
|  |  | U14 | LM311 |
|  |  | U15 | LM311 |
|  |  | U16 | LM311 |
|  |  | U35 | LM311 |
| 51 | 4 | U17 | LF351 |
|  |  | U18 | LF351 |
|  |  | U19 | LF351 |
|  |  | U20 | LF351 |
| 52 | 1 | U25 | LM2931T |
| 53 | 5 | U26 | IH5141 |
|  |  | U28 | IH5141 |
|  |  | U29 | IH5141 |
|  |  | U30 | IH5141 |
|  |  | U31 | IH5141 |
| 54 | 1 | U34 | 4538 |
| 55 | 1 | U36 | 74HC74 |
| 56 | 1 | U37 | 74HC04 |

Figure 13:
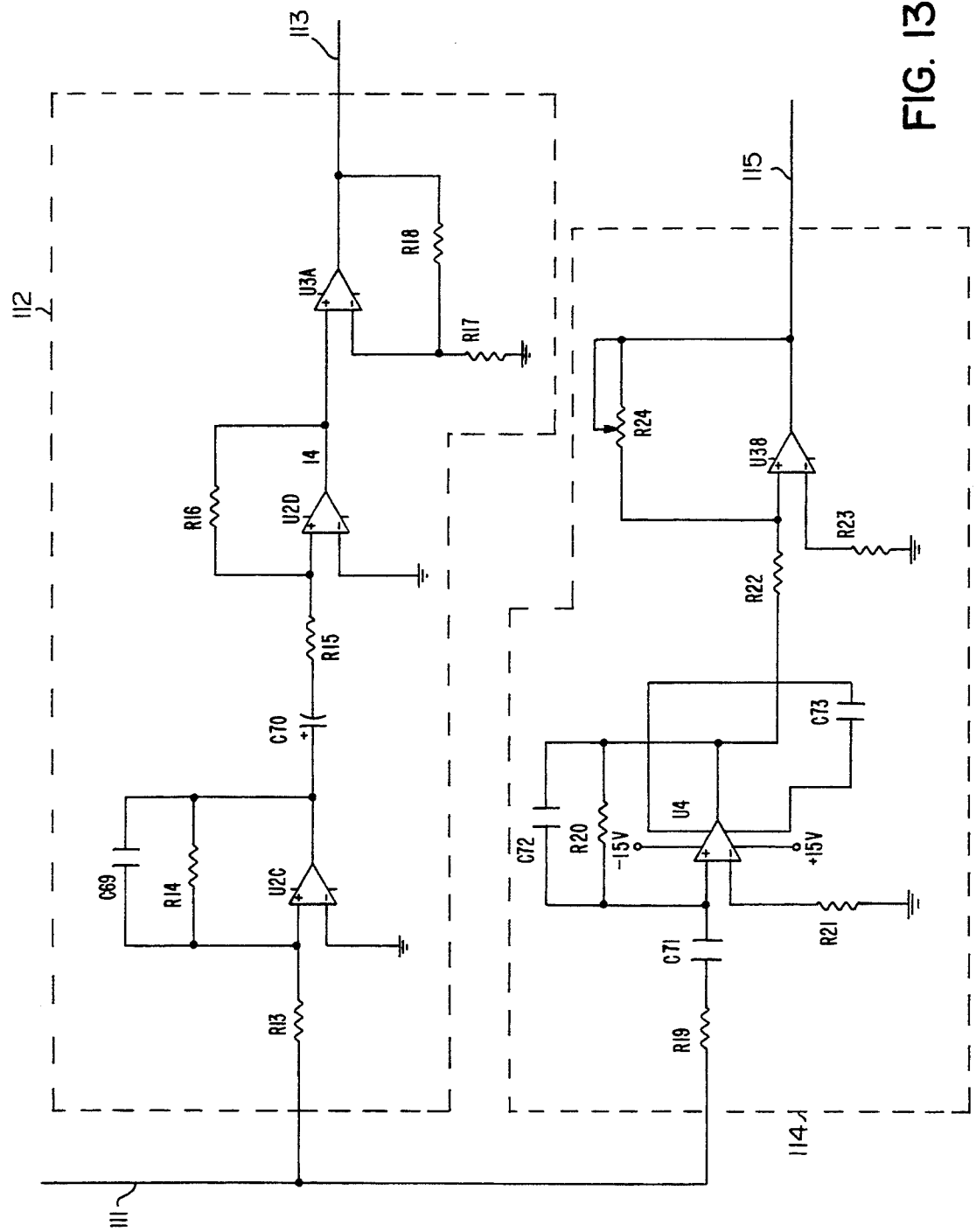
FIG. 13 is a schematic diagram of the bandpass filter and the differentiator from the block diagram of FIG. 6.
Figure 14:
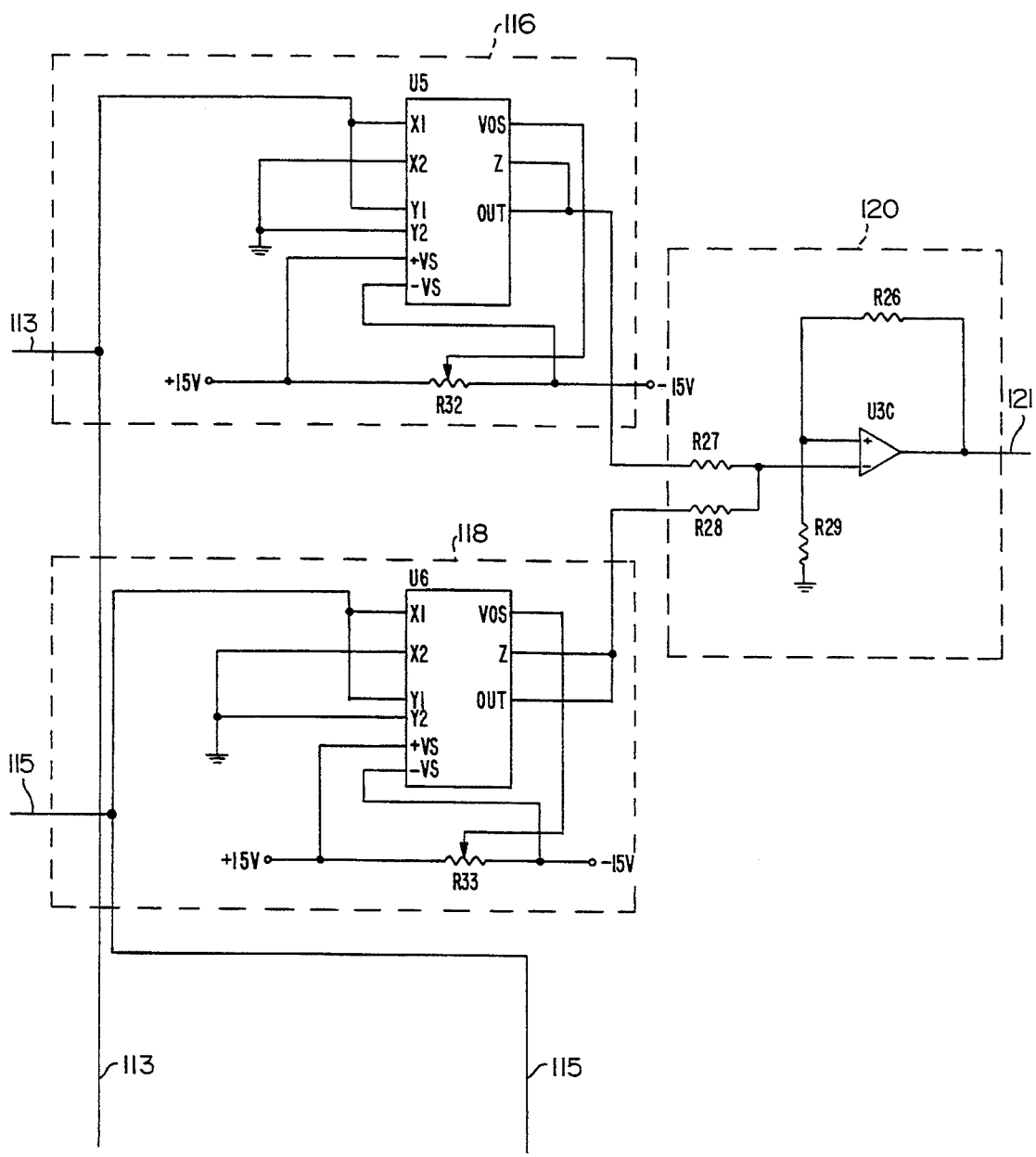
FIG. 14 is a schematic diagram of the squaring circuits and adder from the block diagram of FIG. 6.
Figure 15:
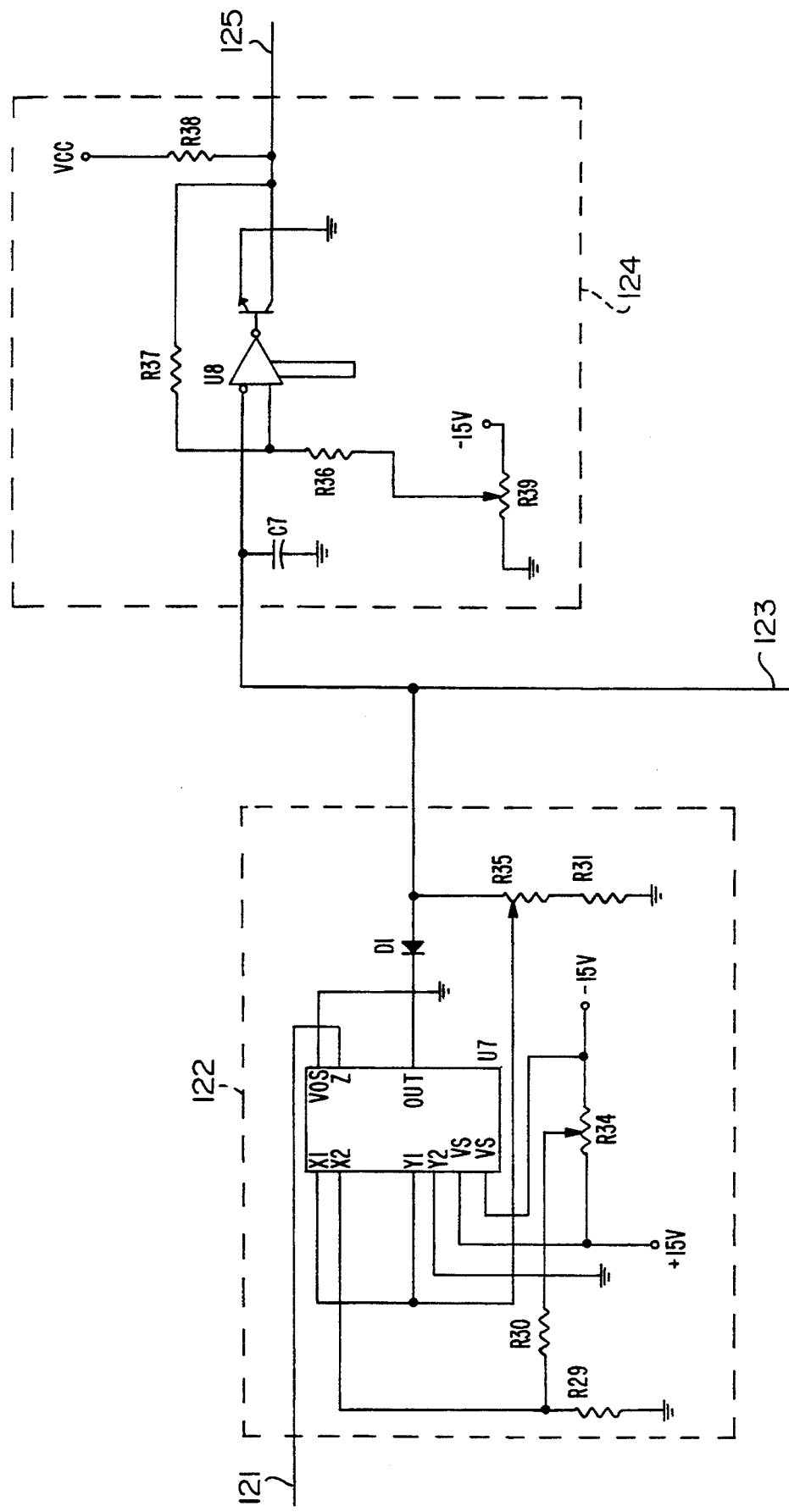
FIG. 15 is a schematic diagram of the square root circuit and comparator with hysteresis from the block diagram of FIG. 6.
Figure 16:
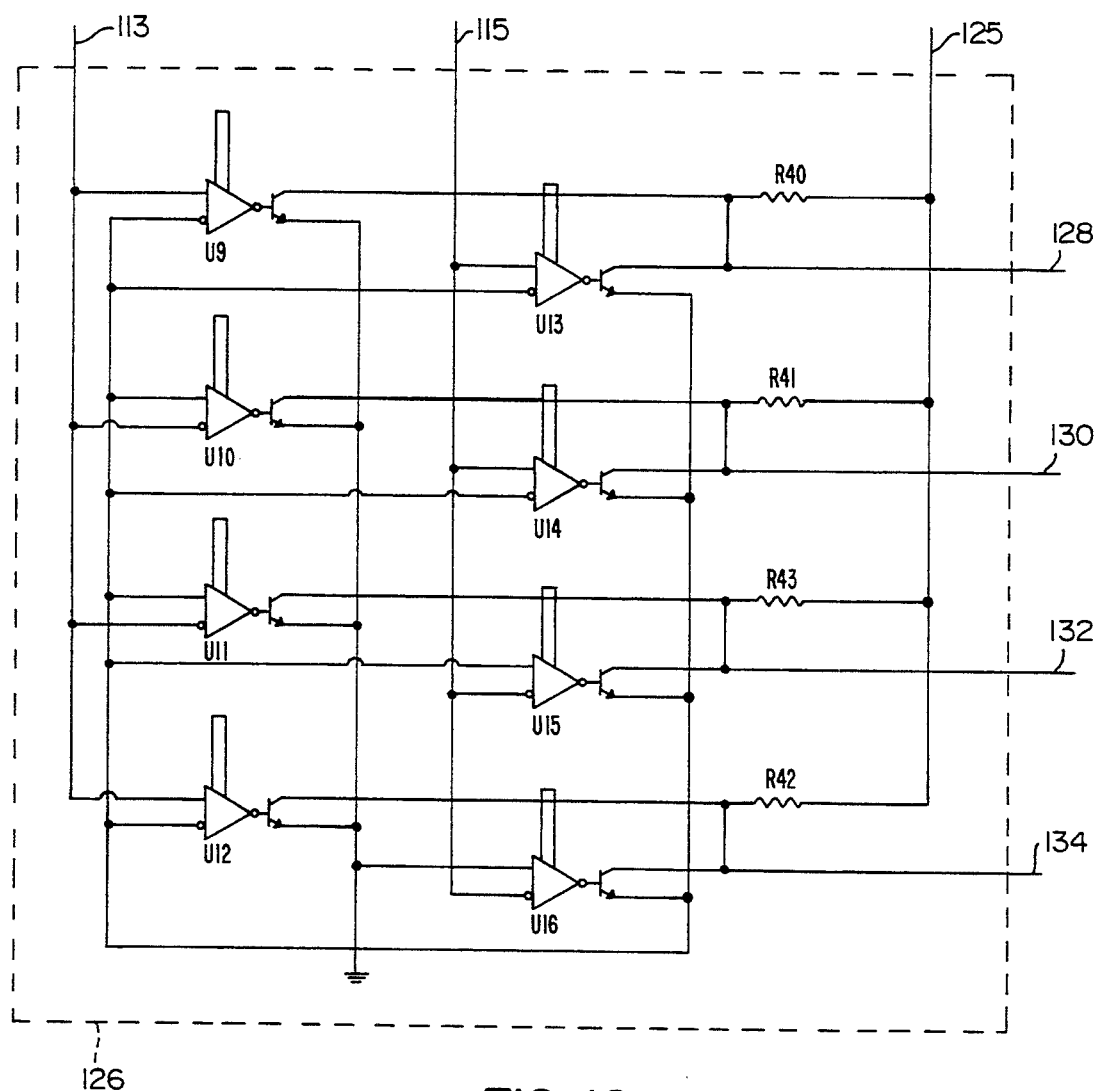
FIG. 16 is a schematic diagram of the quadrant detector from the block diagram of FIG. 6.
Figure 17:
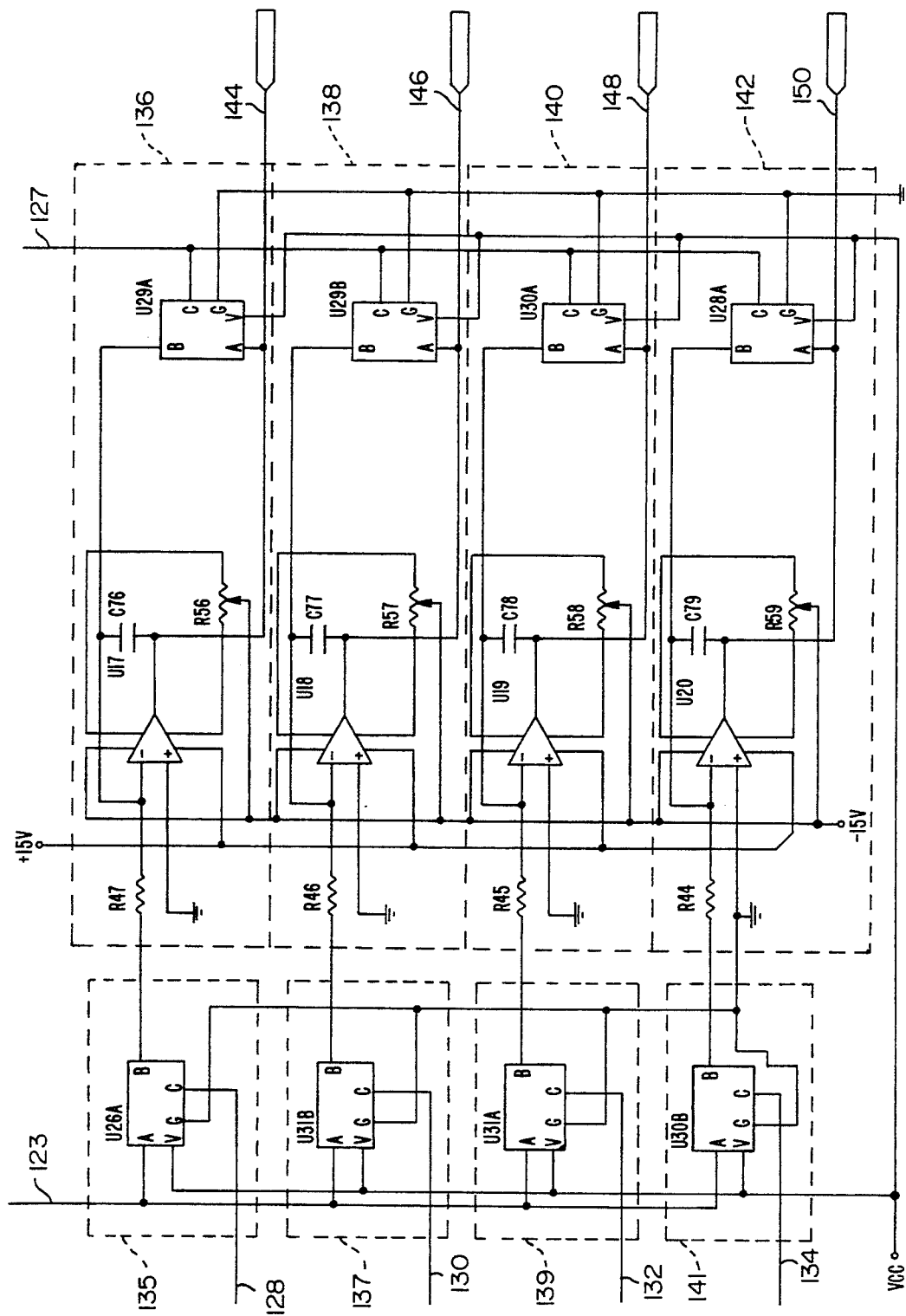
FIG. 17 is a schematic diagram of the switches and integrators from the block diagram of FIG. 6.
Figure 18:
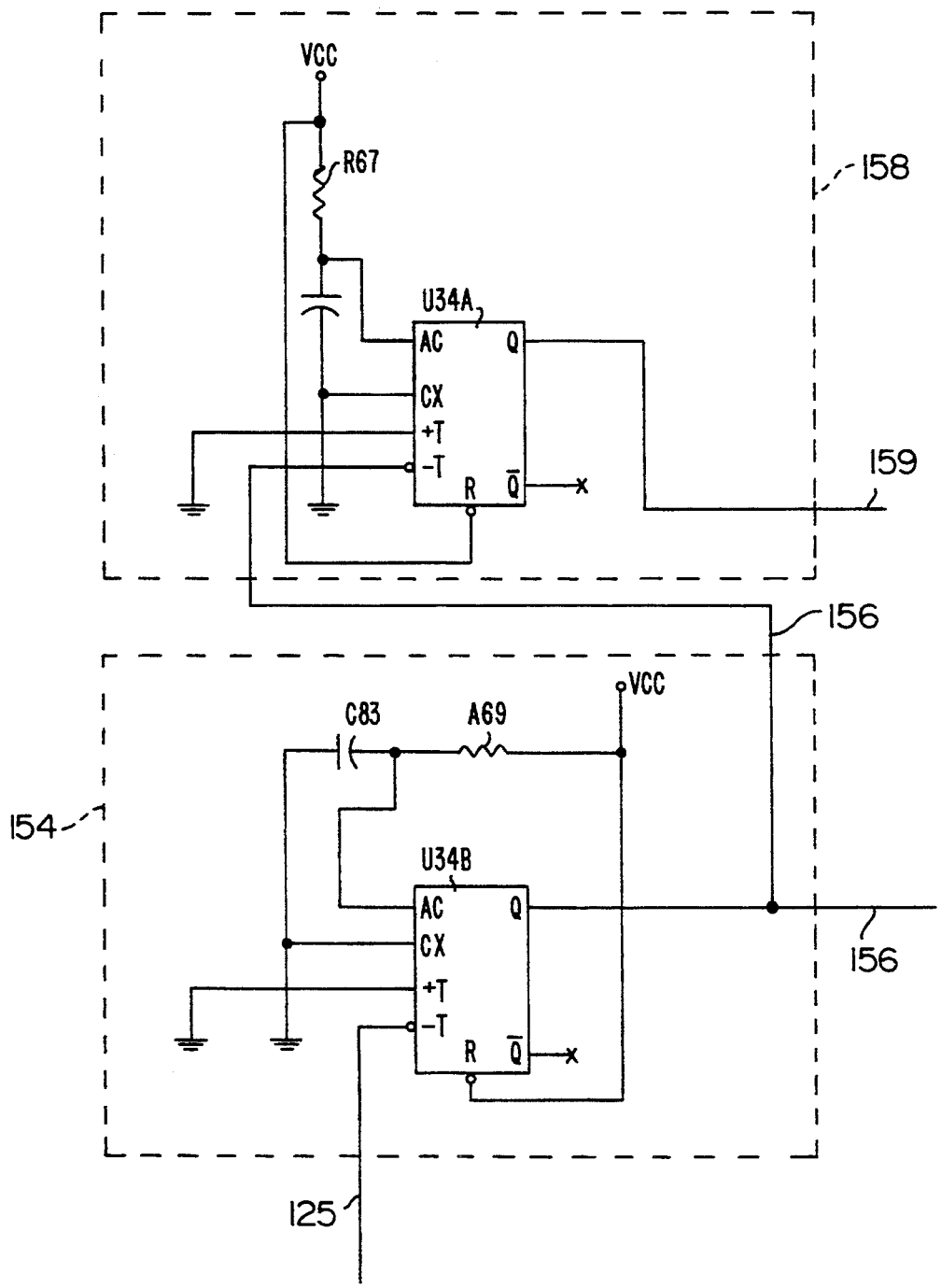
FIG. 18 is a schematic diagram of the valid data circuit and reset circuit from the block diagram of FIG. 6.
Figure 19:
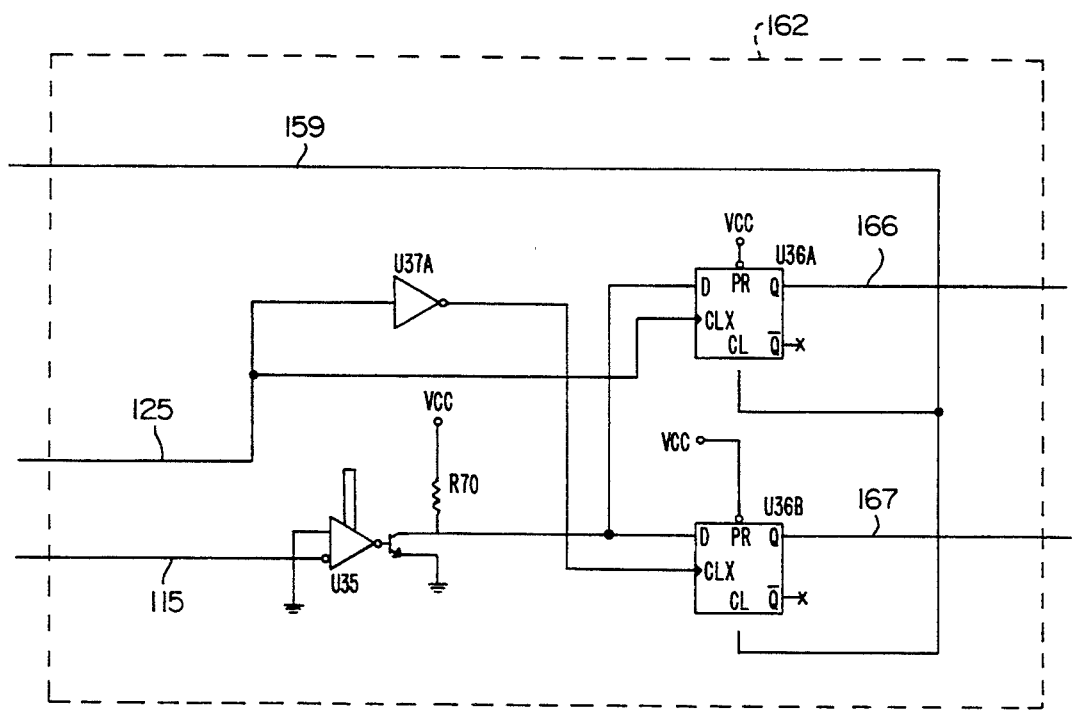
FIG. 19 is a schematic diagram of the initial/final sign detector from the block diagram of FIG. 6.

In FIG. 12, there is shown a schematic diagram of one implementation of bandpass filter and amplifier 110 from the block diagram of FIG. 6. FIG. 13 shows a schematic diagram of one implementation of bandpass filter 112 and differentiator 114 from the block diagram of FIG. 6. FIG. 14 shows squaring circuits 116 and 118, and summing circuit 120 from the block diagram of FIG. 6. FIG. 15 is a schematic diagram of one implementation of square root circuit 122, and comparator with hysteresis 124 from the block diagram of FIG. 6. FIG. 16 shows a schematic diagram of one implementation of quadrant detector circuit 126 from the block diagram of FIG. 6. FIG. 17 is a schematic of switches 135, 137, 139, and 141, and integrators 136, 138, 140, and 142 from the block diagram of FIG. 6, and FIG. 18 shows a schematic diagram of one implementation of valid data circuit 154 and reset circuit 158 from the block diagram of FIG. 6. FIG. 19 is a schematic of initial/final sign detector 162 from the block diagram of FIG. 6.

From the foregoing detailed description of a particular embodiment of the invention, it should be apparent that a method and apparatus for conducting phase plane analysis of EGM signals has been disclosed. It is believed that the presently disclosed invention may be advantageously implemented within an implantable pacemaker, cardioverter, defibrillator or the like, in order to enhance the event-discriminating capability of the implantable device. One pacemaker in which the present invention may be implemented is that disclosed in U.S. Pat. No. 5,052,388 to Sivula et al., which patent is hereby incorporated by reference in its entirety.

Although a specific embodiment of the invention has been described herein in some detail, this has been done for the purposes of illustration only, and is not intended to be limiting with respect to the scope of the present invention. It is contemplated that various substitutions, alterations, and modifications may be made to the embodiment of the invention described herein, even if such substitutions, alterations, or modifications were not specifically noted herein, without departing from the spirit and scope of the present invention, as defined in the appended claims which follow.

What is claimed is:

1. A method of identifying a cardiac event as being of a specific type, comprising the steps of:

monitoring a patient's EGM signal during a cardiac event;

generating a four quadrant phase plane trajectory representation of said patient's EGM signal during said event;

defining a metric reflecting the relative areas circumscribed by said phase plane trajectory in each said quadrant; and identifying said event as being of said specific type in response to said phase plane trajectory corresponding to said metric;

wherein said generating step comprises:

applying said patient's EGM signal to a filter circuit and to a differentiator circuit to produce a filtered EGM signal and a differentiated EGM signal;

applying said filtered EGM signal to a squaring circuit to produce a filtered, squared signal;

applying said differentiated EGM signal to a squaring circuit to produce a squared, differentiated EGM signal;

summing said squared, differentiated EGM signal and said filtered, squared EGM signal to produce a summation signal;

applying said summation signal to a square root circuit to produce a magnitude signal corresponding to a magnitude component of said phase plane trajectory representation of said patient's EGM signal;

defining said four quadrants of said phase plane trajectory representation;

for each said quadrant, separately integrating said magnitude signal to produce a separate integration signal for each said quadrant; and wherein said identifying step comprises indicating occurrence of an event of said specific type when said integration signals correlate in accordance with said metric.

2. A method for indicating occurrences of a specific type of cardiac event comprising the steps of defining at least one characteristic feature of a patient's EGM signal when said specific type of event occurs and thereafter detecting said at least one characteristic feature of said patient's EGM signal;

wherein said step of defining said at least one characteristic feature comprises defining a metric expressing a correlation of four areas circumscribed by a four quadrant phase plane trajectory;

and wherein said step of detecting said at least one characteristic feature comprises the sub-steps of:

monitoring said patient's EGM signal during a cardiac event;

generating a phase plane representation of said EGM signal, said phase plane representation comprising trajectory in a phase plane having four quadrants, said generating step in turn comprising deriving, from said patient's EGM signal, four integration signals, each one of said four integration signals reflecting an area circumscribed by said phase plane trajectory in one said quadrant of said phase plane representation of said EGM signal; and indicating an occurrence of an event of said specific type when said four integration signals correlate in accordance with said metric.

3. An apparatus for detecting occurrences of a specific type of cardiac event, comprising:

a magnitude signal generating circuit means, responsive to an EGM signal from a patient's heart for generating a magnitude signal corresponding to a phase plane trajectory representation of said EGM signal, said phase plane trajectory representation corresponding to a plot of said EGM signal versus a first derivative of said EGM signal in a phase plane having four quadrants;

first, second, third, and fourth integrator circuits, each associated with a different one of said four phase plane quadrants, each coupled to said magnitude generating circuit, each integrator circuits comprising means for producing an integration signal corresponding to an area circumscribed by said phase plane trajectory in its associated quadrant of said phase plane;

a discriminating circuit, coupled to said first, second, third, and fourth integrator circuits and comprising means responsive to receipt of first, second, third, and fourth integration signals having a predetermined correlation for producing produce an event detected signal indicative of occurrence of a cardiac event of said specific type, wherein said predetermined correlation is predetermined based upon analysis of an said patient's EGM signal during an induced occurrence of said specific event.

4. A method of identifying a cardiac event, comprising the steps of:

applying a patient's EGM signal to an amplifier circuit and to a differentiator circuit to produce an amplified EGM signal and a differentiated EGM signal;

applying said amplified EGM signal to a squaring circuit to produce a squared, amplified EGM signal;

applying said differentiated EGM signal to a squaring circuit to produce a squared, differentiated EGM signal;

summing said squared, differentiated EGM signal and said squared, amplified EGM signal to produce a summation signal;

applying said summation signal to a square root circuit to produce a magnitude signal;

separately integrating said magnitude signal (a) while said differentiated EGM signal is positive and said amplified EGM signal is positive, (b) while said differentiated EGM signal is negative and said amplified EGM signal is positive, (c) while said differentiated EGM signal is positive and said amplified EGM signal is negative, and (d) while said differentiated EGM signal is negative and said amplified EGM signal is negative, to produce four separate integration signals; and identifying said event as a function of relative magnitudes of said integration signals.

5. A method of identifying a cardiac event, comprising the steps of:

applying a patient's EGM signal to an amplifier circuit and to a differentiator circuit to produce an amplified EGM signal and a differentiated EGM signal;

combining said amplified EGM signal and said differentiated EGM signal to produce a magnitude signal;

separately integrating said magnitude signal (a) while said differentiated EGM signal is positive and said amplified EGM signal is positive, (b) while said differentiated EGM signal is negative and said amplified EGM signal is positive, (c) while said differentiated EGM signal is positive and said amplified EGM signal is negative, and (d) while said differentiated EGM signal is negative and said amplified EGM signal is negative, to produce four separate integration signals; and identifying said event as a function of relative magnitudes of said integration signals.

6. A method of identifying a cardiac event, comprising the steps of: applying a patient's EGM signal to an amplifier circuit and to a differentiator circuit to produce an amplified EGM signal and a differentiated EGM signal;

applying said amplified EGM signal to a squaring circuit to produce a squared, amplified EGM signal;

applying said differentiated EGM signal to a squaring circuit to produce a squared, differentiated EGM signal;

summing said squared, differentiated EGM signal and said squared, amplified EGM signal to produce a summation signal;

applying said summation signal to a square root circuit to produce a magnitude signal;

separately integrating said magnitude signal while said differentiated EGM signal meets a first predefined criterion and said amplified EGM meets a second predefined criterion to produce an integration signal; and identifying said event as a function of magnitude of said integration signal.

7. A method of identifying a cardiac event, comprising the steps of:

applying a patient's EGM signal to an amplifier circuit and to a differentiator circuit to produce an amplified EGM signal and a differentiated EGM signal;

combining said amplified EGM signal and said differentiated EGM signal to produce a magnitude signal;

separately integrating said magnitude signal while said differentiated EGM signal meets a first predefined criterion and said amplified EGM signal meets a second predefined criterion to produce an integration signal; and identifying said event as a function of magnitude of said integration signal.

8. Apparatus for identifying a cardiac event, comprising:

means for sensing a patient's EGM signal;

amplifier means, coupled to said sensing means, for producing an amplified EGM signal;

differentiator means, coupled to said sensing means, for producing a differentiated EGM signal;

first squaring means, coupled to said filter means, for producing a filtered, squared signal;

second squaring means, coupled to said differentiator means, for producing a squared, differentiated EGM signal;

summing means, coupled to said first and second squaring means, for summing said squared, differentiated EGM signal and said filtered, squared EGM signal to produce a summation signal;

square root determining means, coupled to said summing means, for producing a magnitude signal;

means for separately integrating said magnitude signal (a) while said differentiated EGM signal is positive and said amplified EGM signal is positive, (b) while said differentiated EGM signal is negative and said amplified EGM signal is positive, (c) while said differentiated EGM signal is positive and said amplified EGM signal is negative, and (d) while said differentiated EGM signal is negative and said amplified EGM signal is negative, to produce four separate integration signals; and means for identifying said event as a function of relative magnitudes of said integration signals.

9. Apparatus for identifying a cardiac event, comprising:

means for sensing a patient's EGM signal;

amplifier means, coupled to said sensing means, for producing an amplified EGM signal;

differentiator means, coupled to said sensing means, for producing a differentiated EGM signal;

means for combining said amplified and differentiated EGM signals to produce a magnitude signal;

means for separately integrating said magnitude signal (a) while said differentiated EGM signal is positive and said amplified EGM signal is positive, (b) while said differentiated EGM signal is negative and said amplified EGM signal is positive, (c) while said differentiated EGM signal is positive and said amplified EGM signal is negative, and (d) while said differentiated EGM signal is negative and said amplified EGM signal is negative, to produce four separate integration signals; and means for identifying said event as a function of relative magnitudes of said integration signals.

10. Apparatus for identifying a cardiac event, comprising:

means for sensing a patient's EGM signal;

amplifier means, coupled to said sensing means, for producing an amplified EGM signal;

differentiator means, coupled to said sensing means, for producing a differentiated EGM signal;

first squaring means, coupled to said filter means, for producing a filtered, squared signal;

second squaring means, coupled to said differentiator means, for producing a squared, differentiated EGM signal;

summing means, coupled to said first and second squaring means, for summing said squared, differentiated EGM signal and said filtered, squared EGM signal to produce a summation signal;

square root determining means, coupled to said summing means, for producing a magnitude signal;

means for separately integrating said magnitude signal while said differentiated EGM signal meets a first predefined criterion and said amplified EGM signal meets a second predefined criterion to produce an integration signal; and means for identifying said event as a function of magnitude of said integration signal.

11. Apparatus for identifying a cardiac event, comprising:

means for sensing a patient's EGM signal;

amplifier means, coupled to said sensing means, for producing an amplified EGM signal;

differentiator means, coupled to said sensing means, for producing a differentiated EGM signal;

means for combining said amplified and differentiated EGM signals to produce a magnitude signal;

means for separately integrating said magnitude signal while said differentiated EGM signal meets a first predefined criterion and said amplified EGM signal meets a second predefined criterion to produce an integration signal; and means for identifying said event as a function of magnitude of said integration signal.

* * * * *